(12) United States Patent
Lavi et al.

(10) Patent No.: US 10,441,235 B2
(45) Date of Patent: Oct. 15, 2019

(54) VASCULAR SELECTION FROM IMAGES

(71) Applicant: CathWorks Ltd., Kfar Saba (IL)

(72) Inventors: Guy Lavi, Moshav Mishmeret (IL); Ofek Shilon, Kfar-Saba (IL); Sarit Semo, RaAnana (IL); Omri Harish, Zur Yigal (IL); Asaf Shimshovitz, Rehovot (IL)

(73) Assignee: CathWorks Ltd. (IL)

( * ) Notice: Subject to any disclaimer, the term of this patent is extended or adjusted under 35 U.S.C. 154(b) by 0 days.

(21) Appl. No.: 15/959,024

(22) Filed: Apr. 20, 2018

(65) Prior Publication Data
US 2018/0235561 A1      Aug. 23, 2018

Related U.S. Application Data

(63) Continuation of application No. PCT/IL2017/050544, filed on May 16, 2017.
(Continued)

(51) Int. Cl.
*A61B 6/00* (2006.01)
*G06T 7/12* (2017.01)
(Continued)

(52) U.S. Cl.
CPC ............ *A61B 6/504* (2013.01); *A61B 6/5217* (2013.01); *G06T 7/0012* (2013.01); *G06T 7/11* (2017.01);
(Continued)

(58) Field of Classification Search
CPC . G06T 2207/20076; G06T 2207/20096; G06T 2207/30101; G06T 7/12;
(Continued)

(56) References Cited

U.S. PATENT DOCUMENTS

| 5,150,292 A | 9/1992 | Hoffmann et al. |
| 5,638,823 A | 6/1997 | Akay et al. |

(Continued)

FOREIGN PATENT DOCUMENTS

| EP | 2633815 | 9/2013 |
| WO | 2007/066249 | 6/2007 |

(Continued)

OTHER PUBLICATIONS

Official Action dated May 4, 2017 From the US Patent and Trademark Office Re. U.S. Appl. No. 14/761,079. (19 pages).
(Continued)

*Primary Examiner* — Gregory F Cunningham
(74) *Attorney, Agent, or Firm* — K&L Gates LLP; Louis C. Cullman; Dennis A. Majewski

(57) ABSTRACT

Methods and systems for manually assisted definition of vascular features are described. In some embodiments, vascular centerlines identified by image analysis are divided into segments. Optionally, one or more candidate paths extending to the vascular root position along chains of segments are generated for each of a plurality of vascular endpoint. Selection of paths which correspond to anatomical paths of blood flow is optionally based on manual review. Optionally, paths are manually defined, for example, based on selection of a plurality of waypoints. Optionally, paths are edited by use of an active contour method that allows relative rough indication of corrections to be transformed into path changes that conform closely to the geometry of nearby vasculature.

20 Claims, 8 Drawing Sheets

Related U.S. Application Data

(60) Provisional application No. 62/336,848, filed on May 16, 2016.

(51) Int. Cl.
  G06T 7/149 (2017.01)
  G06T 7/11 (2017.01)
  G06T 7/00 (2017.01)

(52) U.S. Cl.
  CPC .............. G06T 7/12 (2017.01); G06T 7/149 (2017.01); *A61B 6/481* (2013.01); *G06T 2207/20076* (2013.01); *G06T 2207/20096* (2013.01); *G06T 2207/30101* (2013.01)

(58) Field of Classification Search
  CPC ......... G06T 7/0012; G06T 7/11; G06T 7/149; A61B 6/00; A61B 6/504; A61B 6/481
  USPC ....................................................... 382/128
  See application file for complete search history.

(56) References Cited

U.S. PATENT DOCUMENTS

| | | | |
|---|---|---|---|
| 6,047,080 | A | 4/2000 | Chen et al. |
| 6,236,878 | B1 | 5/2001 | Taylor et al. |
| 6,842,638 | B1 | 1/2005 | Suri et al. |
| 7,657,299 | B2 | 2/2010 | Huizenga et al. |
| 7,693,315 | B2 | 4/2010 | Krishnan et al. |
| 7,738,626 | B2 | 6/2010 | Weese et al. |
| 8,090,164 | B2 | 1/2012 | Bullitt et al. |
| 8,298,147 | B2 | 10/2012 | Huennekens et al. |
| 8,311,748 | B2 | 11/2012 | Taylor et al. |
| 8,311,750 | B2 | 11/2012 | Taylor |
| 8,548,778 | B1 | 10/2013 | Hart et al. |
| 8,554,490 | B2 | 10/2013 | Tang et al. |
| 8,560,968 | B1 | 10/2013 | Nair |
| 8,771,195 | B2 | 7/2014 | Kim et al. |
| 8,812,246 | B2 | 8/2014 | Taylor |
| 9,042,613 | B2 | 5/2015 | Spilker et al. |
| 9,078,564 | B2 | 7/2015 | Taylor |
| 9,189,600 | B2 | 11/2015 | Spilker et al. |
| 9,314,584 | B1 | 4/2016 | Riley et al. |
| 9,615,755 | B2 | 4/2017 | Riley et al. |
| 9,754,082 | B2 | 9/2017 | Taylor et al. |
| 9,814,433 | B2 | 11/2017 | Benishti et al. |
| 9,858,387 | B2 | 1/2018 | Lavi et al. |
| 2004/0019264 | A1 | 1/2004 | Suurmond et al. |
| 2004/0066958 | A1 | 4/2004 | Chen et al. |
| 2005/0043614 | A1 | 2/2005 | Huizenga et al. |
| 2006/0036167 | A1* | 2/2006 | Shina ....................... A61B 6/12 600/433 |
| 2007/0167833 | A1 | 7/2007 | Redel et al. |
| 2008/0020362 | A1 | 1/2008 | Cotin et al. |
| 2009/0312648 | A1* | 12/2009 | Zhang ..................... A61B 6/541 600/483 |
| 2010/0017171 | A1 | 1/2010 | Spilker et al. |
| 2010/0067760 | A1 | 3/2010 | Zhang et al. |
| 2010/0160764 | A1 | 6/2010 | Steinberg et al. |
| 2010/0220917 | A1 | 9/2010 | Steinberg et al. |
| 2010/0296709 | A1* | 11/2010 | Ostrovsky-Berman ...................... G06T 7/11 382/128 |
| 2010/0298719 | A1 | 11/2010 | Thrysoe et al. |
| 2011/0015530 | A1 | 1/2011 | Misawa |
| 2011/0096907 | A1 | 4/2011 | Mohamed |
| 2011/0142313 | A1 | 6/2011 | Pack et al. |
| 2011/0182492 | A1 | 7/2011 | Grass et al. |
| 2012/0041318 | A1 | 2/2012 | Taylor |
| 2012/0041739 | A1 | 2/2012 | Taylor |
| 2012/0053918 | A1 | 3/2012 | Taylor |
| 2012/0053921 | A1 | 3/2012 | Taylor |
| 2012/0059246 | A1 | 3/2012 | Taylor |
| 2012/0062841 | A1* | 3/2012 | Stetson ................... A61B 3/102 351/206 |
| 2012/0072190 | A1 | 3/2012 | Sharma et al. |
| 2012/0150048 | A1 | 6/2012 | Kang et al. |
| 2012/0177275 | A1 | 7/2012 | Suri |
| 2012/0230565 | A1 | 9/2012 | Steinberg et al. |
| 2013/0060133 | A1 | 3/2013 | Kassab et al. |
| 2013/0094745 | A1 | 4/2013 | Sundar |
| 2013/0226003 | A1 | 8/2013 | Edic et al. |
| 2013/0229621 | A1 | 9/2013 | Stetson et al. |
| 2013/0324842 | A1 | 12/2013 | Mittal et al. |
| 2014/0094693 | A1 | 4/2014 | Cohen et al. |
| 2014/0303495 | A1 | 10/2014 | Fonte et al. |
| 2015/0201897 | A1 | 7/2015 | Kyriakou |
| 2015/0265162 | A1 | 9/2015 | Lavi et al. |
| 2015/0335304 | A1 | 11/2015 | Lavi et al. |
| 2015/0342551 | A1 | 12/2015 | Lavi et al. |
| 2016/0007945 | A1 | 1/2016 | Taylor |
| 2016/0110866 | A1 | 4/2016 | Taylor |
| 2016/0110867 | A1 | 4/2016 | Taylor |
| 2016/0128661 | A1 | 5/2016 | Taylor |
| 2016/0247279 | A1 | 8/2016 | Lavi et al. |
| 2016/0371456 | A1 | 12/2016 | Taylor et al. |
| 2018/0075221 | A1* | 3/2018 | Vergaro ................ G16H 15/00 |

FOREIGN PATENT DOCUMENTS

| | | |
|---|---|---|
| WO | 2010/033971 | 3/2010 |
| WO | 2014/064702 | 5/2014 |
| WO | 2014/111927 | 7/2014 |
| WO | 2014/111929 | 7/2014 |
| WO | 2014/111930 | 7/2014 |
| WO | 2015/059706 | 4/2015 |
| WO | 2017/199245 | 11/2017 |
| WO | 2017/199246 | 11/2017 |

OTHER PUBLICATIONS

Official Action dated Nov. 7, 2016 From the US Patent and Trademark Office Re. U.S. Appl. No. 14/761,079. (37 pages).

Official Action dated Mar. 2, 2018 From the US Patent and Trademark Office Re. U.S. Appl. No. 14/761,064. (11 pages).

Pellot et al. "A 3D Reconstruction of Vascular Structures From Two X-Ray Angiograms Using an Adapted Simulated Annealing Algorithm", IEEE Transactions on Medical Imaging, 13(1): 48-60, Mar. 1994.

Pinho et al. "Assessment and Stenting of Tracheal Stenosis Using Deformable Shape Models", Medical Image Analysis, XP028364939, 15(2): 250-266, Dec. 2, 2010.

Sarwal et al., "3-D Reconstruction of Coronary Arteries." Proceedings of the 16th Annual International Conference of the IEEE Engineering in Medicine and Biology Society, Engineering Advances: New Opportunities for Biomedical Engineers, Nov. 3, 1994, pp. 504-505.

Seifalian et al. "A New Algorithm for Deriving Pulsatile Blood Flow Waveforms Tested Using Simulated Dynamic Angiographic Data", Neuroradiology, 31: 263-269, 1989.

Seifalian et al. "Blood Flow Measurements Using 3D Distance Concentration Functions Derived From Digital X-Ray Angiograms", Cardiovascular Imaging, Chap.33: 425-442, 1996.

Seifalian et al. "Validation of a Quantitative Radiographic Technique to Estimate Pulsatile Blood Flow Waveforms Using Digital Subtraction Angiographic Data", Journal of Biomedical Engineering, 13(3): 225-233, May 1991.

Shpilfoygel et al. "Comparison of Methods for Instantaneous Angiographic Blood Flow Measurement", Medical Physics, 26(6): 862-871, Jun. 1999.

Sianos et al., The SYNTAX Score: An Angiographic Tool Grading the Complexity of Coronary Artery Disease. EuroIntervention, XP055392801, 1(2):219-227, Aug. 2005.

Siogkas et al. "Quantification of the Effect of Percutaneous Coronary Angioplasty on a Stenosed Right Coronary Artery", 2010 10th IEEE International Conference on Information Technology and Applications in Biomedicine, ITAB 2010, Corfu, Greece, Nov. 3-5, 2010, p. 1-4, Nov. 2010. Abstract.

(56) References Cited

OTHER PUBLICATIONS

Slomka et al. "Fully Automated Wall Motion and Thickening Scoring System for Myocardial Perfusion SPECT: Method Development and Validation in Large Population", Journal of Nuclear Cardiology, XP002718797, 19(2): 291-302, Jan. 26, 2012.
Sprague et al. "Coronary X-Ray Angiographic Reconstruction and Image Orientation", Medical Physics, 33(3): 707-718, Mar. 2006.
Sun, Zhonghua, G. H. Choo, and K. H. Ng. "Coronary CT angiography: current status and continuing challenges." The British Journal of radiology 85.1013 (2012). pp. 495-510.
Takarada et al. "An Angiographic Technique for Coronary Fractional Flow Reserve Measurement: In Vivo Validation", International Journal of Cardiovascular Imaging, International Journal of Cardiovascular Imaging, Published Online, p. 1-10, Aug. 31, 2012.
Termeer et al. "Visualization of Myocardial Perfusion Derived From Coronary Anatomy", IEEE Transactions on Visualization and Computer Graphics, 14(6):1595-1602, Nov./Dec. 2008.
Third-Party Submission filed on Feb. 1, 2016 From the US Patent and Trademark Office Re. U.S. Appl. No. 14/040,688.
Third-Party Submission filed on Feb. 2, 2016 From the US Patent and Trademark Office Re. U.S. Appl. No. 14/437,205.
Third-Party Submission filed on Jun. 14, 2016 From the US Patent and Trademark Office Re, U.S. Appl. No. 14/437,205.
Third-Party Submission filed on Jan. 28, 2016 From the US Patent and Trademark Office Re. U.S. Appl. No. 14/761,064.
Third-Party Submission filed on Jan. 28, 2016 From the US Patent and Trademark Office Re. U.S. Appl. No. 14/761,086.
Third-Party Submission Under 37 CFR 1.290 dated Oct. 19, 2015 From the US Patent and Trademark Office Re. U.S. Appl. No. 14/040,688.
Third-Party Submission Under 37 CFR 1.290 filed on Jun. 14, 2016 From the US Patent and Trademark Office Re. U.S. Appl. No. 14/761,064.
Third-Party Submission Under 37 CFR 1.290 filed on Jun. 14, 2016 From the US Patent and Trademark Office Re. U.S. Appl. No. 14/761,086.
Tomasello et al. "Quantitative Coronary Angiography in the Interventional Cardiology", Advances in the Diagnosis of Coronary Atherosclerosis, Chap. 14:255-272, Nov. 2011.
Translation of Notification of Office Action dated Mar. 7, 2017 From the State Intellectual Property Office of the People's Republic of China Re. Application No. 201480014756.X. (4 Pages).
Tu et al., Assessment of obstruction length and optimal viewing angle from biplane X-ray angiograms. Int. J. Cardiovasc. Imaging, 26:5-17 (2010).
Tu et al., In vivo assessment of optimal viewing angles from X-ray coronary angiography. EuroIntervention, 7:112-120 (2011).
Tu et al., The impact of acquisition angle differences on three-dimensional quantitative coronary angiography. Catheterization and Cardiovascular Interventions, 78(2):214-222 (2011).
Tu et al., In vivo assessment of bifucation optimal viewing angles and bifurcation angles by three-dimensional (3D) quantitative coronary angiography. Int. J. Cardiovasc. Imaging, (2011).
Tuinenburg et al. "Dedicated Bifurcation Analysis: Basic Principles", International Journal of Cardiovascular Imaging, 27: 167-174,2011.
USPTO Communication dated Feb. 8, 2016 Re Third-Party Submission From the US Patent and Trademark Office Re. U.S. Appl. No. 14/761,064.
USPTO Communication dated Feb. 8, 2016 Re Third-Party Submission From the US Patent and Trademark Office Re. U.S. Appl. No. 14/761,086.
USPTO Communication dated Feb. 9, 2016 Re Third-Party Submission From the US Patent and Trademark Office Re. U.S. Appl. No. 14/040,688.
USPTO Communication dated Feb. 19, 2016 Re Third-Party Submission From the US Patent and Trademark Office Re. U.S. Appl. No. 14/437,205.
USPTO Communication dated Jun. 22, 2016 Re Third-Party Submission From the US Patent and Trademark Office Re. U.S. Appl. No. 14/437,205.
USPTO Communication dated Jun. 22, 2016 Re Third-Party Submission From the US Patent and Trademark Office Re. U.S. Appl. No. 14/761,086.
USPTO Communication dated Jun. 22, 2016 Re Third-Party Submission From the US Patent and Trademark Office Re. U.S. Appl. No. 14/7761,064.
Voci et al. "Coronary Flow: A New Asset for the Echo Lab?", European Heart Journal, 25: 1867-1879,2004.
Weickert "Anisotropic Diffusion in Image Processing", ECMI, Published by Teubner, Stuttgart, Germany, 184 P., 2008.
Weickert et al. "A Scheme for Coherence-Enhancing Diffusion Filtering With Optimized Rotation Invariance", Computer Vision, Graphics, and Pattern Recognition Group, CVGPR Group, Technical Report, Computer Science Series, Apr. 2000: Feb. 1-20, 2000.
Weickert et al. "A Scheme for Coherence-Enhancing Diffusion Filtering With Optimized Rotation Invariance", Journal of Visual Communication and Image Representation, 13(1-2): 103-118, Mar. 2002. & Computer Vision, Graphics, and Pattern Recognition Group, CVGPR, Computer Science Series, Technical Report Apr. 2000, Feb. 2000.
Wong et al. "Quantification of Fractional Flow Reserve Based on Angiographic Image Data", International Journal of Cardiovascular Imaging, XP0350 12993, 28(1): 13-22, Published Online Jan. 7, 2011. Abstract, Section Angiographic BasedFFR.
Wong et al. "Determination of Fractional Flow Reserve (FFR) Based on Scaling Laws: A Simulation Study", Physics in Medicine and Biology, 53: 3995-4011, 2008.
Wong et al., Automated technique for angiographic determination of coronary blood flow and lumen volume. Acad. Radiol., 13:186-194 (2006).
Yang et al. "Novel Approach for 3-D Reconstruction of Coronary Arteries From Two Uncalibrated Angiographic Images." IEEE Transactions on Image Processing, vol. 18, No. 7, Jul. 2009, pp. 1563-1572.
Youssef et al., "Role of Computed Tomography Coronary Angiography in the Detection of Vulnerable Plaque, Where Does It Stand Among Others?", Angiology, 1(2): 1000111-1-1000111-8, 2013.
Zhang et al., Quantification of coronary microvascular resistance using angiographic images for volumetric blood flow measurement: in vivo validation. Am. J. Physiol. Heart Circ. Physiol., 300(6):H2096-H2104 (2011).
Andriotis et al. "A New Method of Three-Dimensional Coronary Artery Reconstruction From X-Ray Angiography: Validation Against a Virtual Phantom and Multislice Computed Tomography", Catheterization and Cardiovascular Interventions, 71(1): 28-43, Jan. 1, 2008.
Applicant-Initiated Interview Summary dated Oct. 4, 2016 From the US Patent and Trademark Office Re U.S. Appl. No. 14/040,688.
Applicant-Initiated Interview Summary dated Dec. 23, 2016 From the US Patent and Trademark Office Re. U.S. Appl. No. 14/761,079 (3 pages).
Barratt et al. "Reconstruction and Quantification of the Carotid Artery Bifurcation From 3-D Ultrasound Images", IEEE Transactions on Medical Imaging, XP011112233, 23(5): 567-583,May 1, 2004.
Bullitt et al. "Determining Malignancy of Brain Tumors by Analysis of Vessel Shape", Medical Image Computing and Computer-Assisted Intervention, MICCAI 2004 Conference Proceedings, Lecture Notes in Computer Science, LNCS, 3217:645-653, 2004.
Caiati et al. "New Noninvasive Method for Coronary Flow Reserve Assessment: Contrast-Enhanced Transthoracic Second Harmonic Echo Doppler", Circulation, 99: 771-778, 1999.
Caiati et al. "Detection, Location, and Severity Assessment of Left Anterior Descending Coronary Artery Stenoses by Means of Contrast-Enhanced Transthoracic Harmonic Echo Doppler", European Heart Journal, 30: 1797-1806, 2009.
Communication Relating to the Results of the Partial International Search dated Feb. 6, 2015 From the International Searching Authority Re. Application No. PCT/IL2014/050923.

(56) References Cited

OTHER PUBLICATIONS

Communication Relating to the Results of the Partial International Search dated Jan. 30, 2014 From the International Searching Authority Re. Application No. PCT/IL2013/050869.
Communication Pursuant to Article 94(3) EPC dated Jul. 28, 2017 From the European Patent Office Re. Application No. 13796169.4. (8 Pages).
Communication Pursuant to Article 94(3) EPC dated Aug. 1, 2017 From the European Patent Office Re. Application No. 14710059.8. (7 Pages).
Communication Pursuant to Article 94(3) EPC dated Aug. 3, 2017 From the European Patent Office Re. Application No. 14708097.2. (7 Pages).
Frangi et al. "Multiscale Vessel and Enhancement Filtering", Medical Image Computing and Computer-Assisted Intervention, MICCA'98, Lecture Notes in Computer Science, 1496: 130-137, 1998.
Fusejima "Noninvasive Measurement of Coronary Artery Blood Flow Using Combined Two-Dimensional and Doppler Echocardiography", Journal of the American College of Cardiology, JACC, 10(5): 1024-1031, Nov. 1987.
Hawkes et al. "Validation of Volume Blood Flow Measurements Using Three-Dimensional Distance-Concentration Functions Derived From Digital X -Ray Angiograms", Investigative Radiology, 29(4): 434-442, Apr. 1994.
Hoffmann et al. "Determination of Instantaneous and Average Blood Flow Rates From Digital Angiograms of Vessel Phantoms Using Distance-Density Curves", Investigative Radiology, 26(3): 207-212, Mar. 1991.
Holdsworth et al. "Quantitative Angiographic Blood-Flow Measurement Using Pulsed Intra-Arterial Injection", Medical Physics, 26(10): 2168-2175, Oct. 1999.
Huo, Yunlong, and Ghassan S. Kassab. "Intraspecffic scaling laws of vascular trees." Journal of The Royal Society Interface 9.66 (2012). pp. 190-200.
International Preliminary Report on Patentability dated Jul. 30, 2015 From the International Bureau of WIPO Re. Application No. PCT/IL2014/050044.
International Preliminary Report on Patentability dated May 6, 2016 From the International Bureau of WIPO Re. Application No. PCT/IL2014/050923.
International Preliminary Report on Patentability dated May 7, 2015 From the International Bureau of WIPO Re. Application No. PCT/IL2013/050869.
International Preliminary Report on Patentability dated Jul. 30, 2015 From the International Bureau of WIPO Re. Application No. PCT/IL2014/050039.
International Preliminary Report on Patentability dated Jul. 30, 2015 From the International Bureau of WIPO Re. Application No. PCT/IL2014/050043.
International Search Report and the Written Opinion dated Jul. 10, 2015 From the International Searching Authority Re. Application No. PCT/IL2014/050923.
International Search Report and the Written Opinion dated May 16, 2014 From the International Searching Authority Re. Application No. PCT/IL2014/050043.
International Search Report and the Written Opinion dated May 16, 2014 From the International Searching Authority Re. Application No. PCT/IL2014/050044.
International Search Report and the Written Opinion dated May 23, 2014 From the International Searching Authority Re. Application No. PCT/IL2013/050869.
International Search Report and the Written Opinion dated May 28, 2014 From the International Searching Authority Re. Application No. PCT/IL2014/050039.

Janssen et al. "New Approaches for the Assessment of Vessel Sizes in Quantitative (Cardio-) Vascular X-Ray Analysis", International Journal of Cardiovascular Imaging, 26: 259-271, 2010.
Kappetein et al. "Current Percutaneous Coronary Intervention and Coronary Artery Bypass Grafting Practices for Three-Vessel and Left Main Coronary Artery Disease. Insights From the SYNTAX Run-h1 Phase", European Journal of Cardio-Thoracic Surgery, 29: 486-491, Aug. 18, 2010.
Kirkeeide "Coronary Obstructions, Morphology and Physiologic Significance", Quantitative Coronary Arteriography, Chap. 11: 229-244, 1991.
Leonardou et al., "Close to transplant renal artery stenosis and percutaneous transluminal treatment." Journal of Transplantation (2011 ). pp. 1-8.
Lethen et al. "Validation of Noninvasive Assessment of Coronary Flow Velocity Reserve in the Right Coronary Artery. A Comparison of Transthoracic Echocardiographic Results With Intracoronary Doppler Flow Wire Measurements" European Heart Journal, 24: 1567-1575, 2003.
Meimoun et al. "Non-Invasive Assessment of Coronary Flow and Coronary Flow Reserve by Transthoracic Doppler Echocardiography: A Magic Tool for the Real World", European Journal of Echocardiography, 9: 449-457, 2008.
Mercer-Rosa et al., "Illustration of the additional value of real-time 3-dimensional echocardiography to conventional transthoracic and transesophageal 2-dimensional echocardiography in imaging muscular ventricular septal defects: Does this have any impact on individual patient treatment?" Journal of the American Society of Echocardiography 19.12 (2006): pp. 1511-1519.
Molloi et al., "Quantification of Fractional Flow Reserve Using Angiographic Image Data", World Congress on Medical Physics and Biomedical Engineering, Munich, Germany, Sep. 7-12, 2009, IFMBE Proceedings, 25/2: 901-904, 2009.
Molloi et al., Estimation of coronary artery hyperemic blood flow based on arterial lumen volume using angiographic images. Int. J. Cardiovasc. Imaging, 28(1):1-11 (2012).
Ng "Novel QCA Methodologies and Angiographic Scores", The International Journal of Cardiovascular Imaging, XP002718798, 27(2): 157-165, Feb. 20, 2011.
Notification of Office Action and Search Report dated Mar. 7, 2017 From the State Intellectual Property Office of the People's Republic of China Re. Application No. 201480014756.X. (6 Pages).
Official Action dated Aug. 15, 2016 From the US Patent and Trademark Office Re. U.S. Appl. No. 14/040,688.
Official Action dated Dec. 23, 2016 From the US Patent and Trademark Office Re. U.S. Appl. No. 14/437,205. (54 pages).
Official Action dated Dec. 24, 2015 From the US Patent and Trademark Office Re. U.S. Appl. No. 14/866,098.
International Search Report and the Written Opinion dated Aug. 24, 2017 From the International Searching Authority Re. Application No. PCT/IL2017/050543.
U.S. Appl. No. 15/809,704, filed Nov. 10, 2017.
Dickie et al., Live-vessel: Interactive vascular image segmentation with simultaneous extraction of optimal medial and boundary paths. Technical report TR 2009-23, School of Computing Science, Simon Fraser University, Burnaby, BC, Canada, Nov. (2009).
International Search Report and Written Opinion dated Oct. 2, 2017 for International Application No. PCT/IL2017/050544.
Kass et al., "Snakes: Active contour models." Int. J. Comput. Vis. (1987), 1:321-331.
Weickert, "Anisotropic Diffusion in Image Processing." ECMI, (1998).
Xu et al.,"Snakes, Shapes, and Gradient Vector Flow." IEEE Transactions on Image Processing (1998), 7:359-369.

\* cited by examiner

VASCULAR SELECTION FROM IMAGES

RELATED APPLICATIONS

The present application is a continuation of International Application No. PCT/IL2017/050544, filed on May 16, 2017, which claims priority to U.S. Provisional Patent Application No. 62/336,848, filed May 16, 2016, the entire contents of each of which are incorporated herein by reference and relied upon.

TECHNICAL FIELD

The present disclosure relates in general to the field of anatomical segmentation and more particularly, to manually assisted segmentation of branched vascular anatomy.

BACKGROUND

Vascular segmentation and feature identification is a preliminary stage of image-based measurement of vascular state. Though many stages of vascular segmentation and feature identification can be performed based primarily on automated analysis, relevant image features are often of low contrast and/or embedded in a complex environment comprising elements of ambiguous geometry and extraneous features. Human supervision may be introduced into the workflow to make corrections and help ensure quality of results, resulting in a semi-automated process, for example as in the Livewire and related procedures (discussed, for example, in Ryan Dickie, et al.; Live-vessel: Interactive vascular image segmentation with simultaneous extraction of optimal medial and boundary paths. Technical report TR 2009-23, School of Computing Science, Simon Fraser University, Burnaby, BC, Canada, November 2009).

Additional background art includes:

an article titled: "Snakes: Active contour models", by M. Kass, A. Witkin, and D. Terzopoulos, published in Int. J. Comput. Vis. (1987), 1:321-331;

an article titled: "Multiscale vessel enhancement filtering", by A. F Frangi, W. J. Niessen, K. L. Vincken, M. A. Viergever, published in Medical Image Computing and Computer-Assisted Intervention-MICCA '98; and an article titled: "Snakes, Shapes, and Gradient Vector Flow", by C. Xu and J. L. Prince, published in IEEE Transactions on Image Processing (1998), 7:359-369.

SUMMARY

There is provided, in accordance with some exemplary embodiments, a method of segmenting a vascular image into vascular paths for defining paths of blood flow. The method includes defining first and second targeted vascular path end regions within the vascular image, identifying the positions of vascular portions in the vascular image, and automatically generating a plurality of vascular path options from the identified vascular portions, each vascular path option defining a potential vascular path which extends between the first and second targeted vascular path end regions. The method may also include displaying the plurality of vascular path options registered to the vascular image for selection by a user, each of the displayed vascular path options including the first and second targeted vascular path end regions. The example method may further include receiving a path option selected by the user for defining a path of blood flow.

According to some embodiments, the plurality of paths are automatically generated based on a first set of criteria, and the path option selected by the user is selected based on a second set of criteria.

According to some embodiments, the predetermining comprises ranking the vascular path options in an order, based on assessment of a likelihood that each vascular path option corresponds to an actual path of blood flow in blood vessels imaged in the vascular image.

According to some embodiments, the predetermining comprises applying a cost function which assigns numerical costs to one or more features related to the vascular path options.

According to some embodiments, the cost function assigns numerical costs based on features of a plurality of vascular segment centerlines from which the vascular path option is concatenated.

According to some embodiments, the features of the plurality of vascular segment centerlines include one or more from the group consisting of: centerline orientation, centerline offset, and a count of centerlines extending from a nodal region.

According to some embodiments, the cost function assigns numerical costs based on features of the vascular image over which the vascular path option extends.

According to some embodiments, the features of the vascular image include one or more of the group consisting of: continuity of vascular segment image intensity, continuity of vascular segment image width, and the position of a relative change in vascular intensity with respect to a nodal region from which three or more vascular segments extend.

According to some embodiments, the predetermining comprises applying a cost function which assigns numerical costs based on an estimated relative position of a vascular segment image in depth, relative to an axis extending perpendicular to a plane of the vascular image.

According to some embodiments, the presenting comprises presenting the plurality of vascular path options in a sequential order determined by the order of selection.

According to some embodiments, the presenting comprises presenting the plurality of vascular path options simultaneously, and the order of selection corresponds to an order in which the vascular path options are displayed as active for selection.

According to some embodiments, each vascular path option defines a vascular path which extends through an image region between the first and second targeted vascular path end regions, ending at a vascular region of the image which is nearest to one of the first and second targeted vascular path end positions.

There is provided, in accordance with some exemplary embodiments, a method of editing a vascular path to more accurately delineate a segmentation of a blood vessel in a vascular image. The example method includes receiving an indication of a selected region along the segmentation of the blood vessel, defining an energy functional defined as a function of position along the segmentation of the blood vessel, wherein non-zero regions of the energy functional are set based on the position of the selected region. The method may also include moving regions of the segmentation in accordance with energy minimization within the non-zero regions of the energy functional.

According to some embodiments, energy functional values in the non-zero regions are set based on features of the underlying vascular image.

According to some embodiments, energy functional values in the non-zero regions are set based on movement of a user-controlled position indication.

According to some embodiments, the user-controlled position indication comprises the indication of the selected region.

There is provided, in accordance with some exemplary embodiments, a user interface for semi-automatic segmentation of a vascular path, the user interface comprising: at least one interface module operable to present an automatically generated default vascular path extending between two target end points; at least one interface module operable to present at least one additional automatically generated vascular path extending between the two target end points.

According to some embodiments, the user interface further comprises at least one interface module allowing definition of at least one way point, and operable to present an automatically generated vascular path extending between the two target end points via the at least one way point.

According to some embodiments, the user interface further comprises at least one interface module operable to modify a previously defined vascular path by dragging a portion of the vascular path to a new location.

Unless otherwise defined, all technical and/or scientific terms used herein have the same meaning as commonly understood by one of ordinary skill in the art to which the disclosure pertains. Although a system, a method, an apparatus, and/or a computer program product similar or equivalent to those described herein can be used in the practice or testing of embodiments disclosed herein, exemplary systems, methods, apparatuses, and/or computer program products are described below. In case of conflict, the patent specification, including definitions, will control. In addition, the systems, methods, apparatuses, computer program products, and examples are illustrative only and are not intended to be necessarily limiting.

As will be appreciated by one skilled in the art, aspects of the present disclosure may be embodied as a system, a method or a computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of the method and/or system of the disclosure, several selected tasks could be implemented by hardware, by software or by firmware and/or by a combination thereof, e.g., using an operating system.

For example, hardware for performing selected tasks according to some embodiments of the disclosure could be implemented as a chip or a circuit. As software, selected tasks according to some embodiments of the disclosure could be implemented as a plurality of software instructions executed by a computer using any suitable operating system. In an exemplary embodiment of the disclosure, one or more tasks, according to some exemplary embodiments of a method and/or a system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection may be provided. A display and/or a user input device such as a keyboard or mouse may also be provided.

Any combination of one or more computer readable medium(s) may be utilized for some embodiments of the disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Additional features and advantages of the disclosed system, method, and apparatus are described in, and will be apparent from, the following Detailed Description and the Figures.

BRIEF DESCRIPTION OF THE DRAWINGS

Some embodiments of the example systems, methods, apparatuses, and/or computer program products are herein described, by way of example only, with reference to the accompanying drawings. With specific reference now to the drawings in detail, it is stressed that the particulars shown are by way of example, and for purposes of illustrative discussion of embodiments of the systems, methods, apparatuses, and/or computer program products. In this regard, the description taken with the drawings makes apparent to those skilled in the art how embodiments of the systems, methods, apparatuses, and/or computer program products may be practiced.

In the drawings.

DETAILED DESCRIPTION

Figure 1:
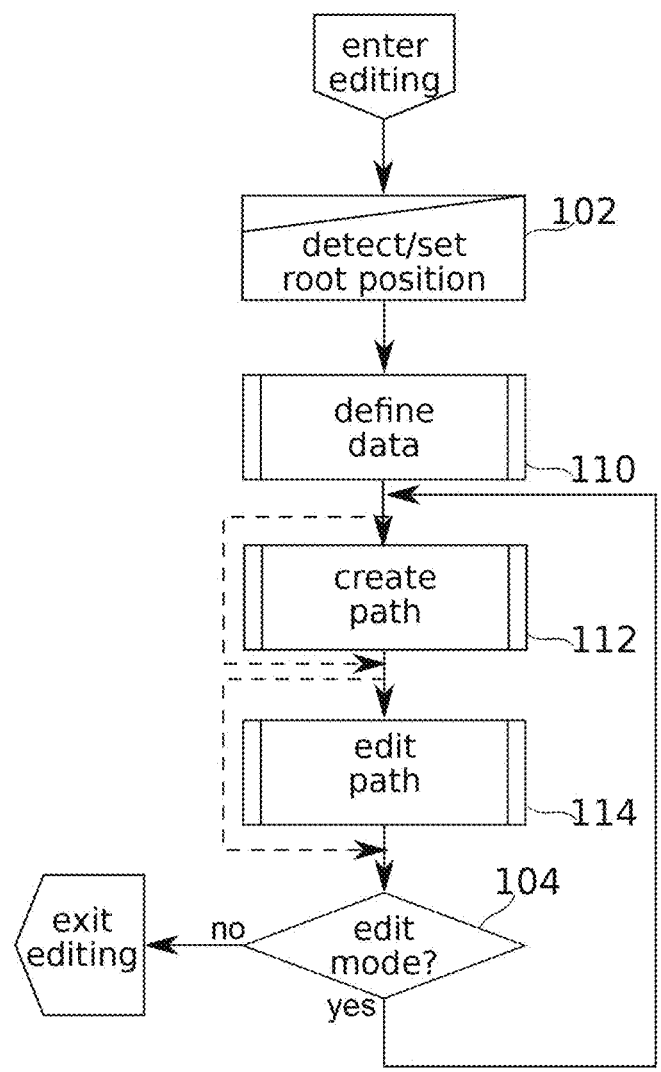
FIG. 1 is a schematic flowchart of a method for defining vascular centerline paths on an angiographic image, according to some exemplary embodiments of the present disclosure.

The present disclosure, in some embodiments thereof, relates to the field of anatomical segmentation and more particularly, to manually assisted segmentation of branched vascular anatomy.

Overview

A broad aspect of some embodiments of the current disclosure relates to methods for combining manual and automatic segmentation techniques, which potentially allows for efficient, reliable vascular tree generation.

Vascular segmentation is an early step in the characterization of vascular anatomy and function from medical image data for a range of applications, including studies of blood flow. However, automatic segmentation methods typically display degraded performance as requirements become more stringent. In addition, contrast agents are limited in their usable concentration; injectable contrast agents quickly dilute, limiting available imaging time. Further, for safety reasons, radiation doses used in some types of imaging are preferably kept to a minimum necessary for reliable visualization. Even though high contrast and/or high signal-to-noise can often be achieved for large blood vessels, there is also a need in some applications to analyze smaller vessels. However, imaging quality rapidly degrades with decreased vascular diameter, as the signal intensity approaches the limit of background noise, or even quantum noise inherent to the signal itself. Apart from these technical considerations, vasculature itself is highly complicated in form. This potentially gives rise, particularly in 2-D images, to many cases of ambiguous structure; difficult to resolve to a particular branch structure by inspection at the level of local features. Global feature detection, on the other hand, is difficult to address by general automatic methods, as interpreting such features potentially relies on particularities of the constraints applicable for a particular structure and/or imaging method.

For these and other reasons, the practical case often results that the quality of medical images available for analysis is, at least for some vascular structures of interest, near or beyond the limits of present techniques for machine vision and/or image processing. Even if the boundaries of these limits should shift over time as technology develops, it is to be expected that there will continue to be interesting segmentation problems for which automatic vascular segmentation alone is inadequate.

Semi-automatic segmentation methods seek to address limitations of purely automatic segmentation methods by augmenting them with human judgement and/or control. However, human intervention is expensive in terms of time, money, and/or availability. In view of this, a goal in some semi-automatic segmentation methods is to reduce human time and/or effort spent in supervising automatic segmentation. Considered as a problem in optimization, the goal, in some embodiments of the disclosure, may be to bring human intervention in semi-automatic segmentation to the lowest achievable level which is consistent with results of sufficiently quality for the use to which they are applied. Accordingly, preferred methods for semi-automatic segmentation may include features which are specific to application in particular problem domains.

An aspect of some embodiments of the present disclosure relates to cascading methods for semi-automatic vascular segmentation of angiographic images. More particularly, in some embodiments, the aspect relates to cascading methods for semi-automatic segmentation of angiographic images while working within the constraints of producing results in real-time. Optionally, segmentation is completed while a catheter procedure, which may be been used to produce the images, is still underway, while leaving sufficient time for subsequent analysis, e.g., analysis leading to diagnosis and/or treatment planning.

In some embodiments, the manually supervised operations of the semi-automatic vascular segmentation are structured to cascade through an increasingly attention-demanding set of user operations, where the cascading is stopped once the user is satisfied that a sufficient quality of result has been obtained. There may be one or more routes through this cascade of operations; for example, the order of operations chosen optionally depends on whether nearly adequate results are obtained early that only need minor editing, or whether a suitable path needs to be defined by a user de novo. In some embodiments, the cascade is structured so that more likely options are presented earlier and/or with greater emphasis, potentially reducing time and/or effort spent by a user in making selections. Optionally, the order of operations is selected to emphasize getting "close enough" results with minimum input, while also providing an opportunity for the correction of errors in automatically identified results as necessary.

In some embodiments, the method optionally starts with the definition of two vascular path end regions (e.g., regions within some maximum distance from a selection point); after which a most-likely and automatically detected path is presented to the user for acceptance or rejection. For a suitable definition of "most-likely" (e.g., a suitable cost function), this potentially allows most or a plurality of user interventions to be limited to simple acceptance of a default. Optionally a plurality of vascular path end region pairs are defined initially, and a corresponding plurality of default options are presented simultaneously, and user interaction is limited still further to correcting defaults. In some embodiments, definition of one of the endpoints is simplified by defining at least one endpoint at a root position of the vascular tree, positioned such that it may be considered to be at one end of any vascular path leading back from one of its branches. In some embodiments, definition of a plurality of vascular terminal positions is based on fully automatic detection (e.g., positions where a vascular skeleton defining vascular centerlines naturally ends), or a semi-automatic method such as positions where a selection line swept out by the user intersects segments of an automatically detected vascular skeletonization.

If a default path is not accepted, in some embodiments, then decreasingly likely (higher cost function scored), automatically suggested paths are optionally presented as available. For example, the user can use a scroll wheel or other control to quickly show alternative paths that extend between some pair of target vascular path end regions.

Failing to find an adequate path among automatically suggested alternatives, in some embodiments, the user is provided with a user interface tool which is operable to define a vascular path based on the definition of one or more additional waypoints.

Additionally or alternatively, one or more editing tools are optionally provided, which allow a nearly-acceptable presented alternative to be modified. For example, a path may be cut, extended, and/or merged with a portion of another existing path. In some embodiments, a path is optionally edited along its length, for example, by re-tracing, redefinition of anchor points, and/or dragging of erroneously segments regions into their correct position.

In some embodiments of the disclosure, a target of the semi-automatic vascular segmentation is the production of one or more vascular paths corresponding to anatomically valid paths of blood flow. In some embodiments, a vascular path comprises a numerically stored sequence of positions corresponding to vascular image positions. In some embodiments, the vascular path comprises a vascular center-line. Optionally, the vascular path is defined at one end by a root position, located at the path end, which is for example, within the least-branched vessel the path traverses. At the other end, the vascular path is optionally defined by a terminal position, which is, for example, located within the most-branched vessel the path traverses.

In some embodiments, vascular paths are defined by the concatenation of one or more vascular segments. Optionally, vascular segments are defined by one or more methods, at one or more levels of fidelity. In some embodiments, a vascular segment may be defined within a skeletonized representation of a vascular image (e.g., a binary pixel-array representation which extends through the detected extent of the vasculature with a one-pixel width). Such a vascular segment optionally comprises a sequence of pixel locations extending between two pixels which mark its end points. The end points are optionally selected by any convenient method, even arbitrarily (e.g., by breaking the skeleton into segments of at most N pixels in length). Preferably, however, vascular segment end points are defined at branches and/or crossings (e.g., skeleton pixels from which branches lead in at least three directions), and/or at free ends (e.g., skeleton pixels from which only one branch leads).

In some embodiments, vascular paths are defined separately from one another. In some embodiments, vascular paths are defined by their different extents along a branched vascular tree (e.g., defined by a particular path of traversing the branches of vascular tree; optionally a vascular tree defined as a set of linked vascular segments). In some embodiments, in contrast, a vascular tree is defined by the merger of a set of vascular paths, e.g., paths which share a common vascular segment are also considered to share a common root segment.

An aspect of some embodiments of the present disclosure relates to methods of selecting vascular paths based on the ordered presentation of automatically generated vascular path options.

In some embodiments of the disclosure, a plurality of path routes extending along detected vascular segments (e.g., vascular segments defined according to criteria of gradient, curvature, and/or relative intensity) are generated for a pair of end regions. Optionally, the generated path routes are those which reach to segment points which are within some region; optionally the region is defined, for example, as the region within some maximum distance from an end-point. This distinction is relevant, for example, in case one of the end points is not itself on a segment.

In some embodiments, the plurality of path routes is presented as a range of vascular path options in a pre-determined order. Optionally, the pre-determined order is based on a cost function constructed to rank path routes according to criteria (optionally, heuristic criteria) that assign more-likely actual paths of blood flow between two end points a lower cost value than less-likely actual paths of blood flow. Preferably, path routes are presented along with image data from which they derive, for example, as graphical overlays on the image. In some embodiments, image data is presented as an animated sequence of images, e.g., images between which the vasculature moves slightly, and/or is viewed from a different angle. Potentially, these differences harness visual capabilities more particular to the user than to the automatic detection algorithm, for example, by emphasizing connectedness among portions of the vasculature which move together.

In some embodiments, cost function criteria include aspects of vascular continuity, vascular branching anatomy, criteria based on the three-dimensional shape of an organ which the vasculature perfuses, vascular image opacity, and/or other criteria.

In some embodiments, automatic segmentation results potentially do not unambiguously distinguish which path, among a plurality of alternative vascular paths between two vascular positions, corresponds to an actual path of blood flow. Particularly in the case of 2-D images of 3-D vascular structures (e.g., vascular structure that is typically visualized extending through two or more layers of depth) branches of the same vascular tree may appear to cross over each other. Although same-tree crossover is seldom observed in structures which are typically imaged within a single focal plane, such as inner retinal vasculature, ambiguities may arise in cases where distinguishing between venous and arterial structures is difficult.

It is noted that dynamic path extending methods, such as Livewire, partially mitigate automatic segmentation ambiguities by allowing the definition of waypoints that can be set to force the automatic result into the correct segmentation. However, this is potentially more time-consuming than simply defining start and end points. In some embodiments, there is a tradeoff between a certain but slow vascular path definition by use of waypoints, and a less certain but potentially faster vascular path definition by selection from among automatically predefined vascular path options.

An aspect of some embodiments of the present disclosure relates to methods of editing vascular paths by dragging an erroneously segmented region into alignment with a more correctly segmented position.

In some embodiments, the method comprises receiving an indication of a selected region along the segmentation of the blood vessel. In some embodiments, the indication comprises a screen coordinate point selection, for example, by pressing a button in conjunction with a particular position of a screen cursor, and/or a gesture input to a touch screen. In some embodiments, the indication comprises directly selecting an erroneously segmented region.

In some embodiments, the method comprises assigning motion susceptibility characteristics to a segmentation path region surrounding the selected region that enable it to be moved, preferably while maintaining the remainder of the segmentation in a state which is not susceptible to movement. In some embodiments, the assigning of susceptibility to motion comprises defining an energy functional defined as a function of position along the segmentation of the blood vessel. Optionally, non-zero regions of the energy functional are set based on the position of the selected region. In some embodiments, the method comprises moving regions of the segmentation in accordance with energy minimization within the non-zero regions of the energy functional. Optionally, motion of the motion-susceptible portion of the segmentation path region is in coordination with movement of a cursor. Optionally, motion of the motion-susceptible portion is at least partially governed by values and/or gradients of image intensity in vicinity of the selected region, such that the selected region behaves as though attracted to vascular regions as it moves.

Before explaining at least one embodiment of the disclosure in detail, it is to be understood that the example systems, methods, apparatuses, and/or computer program products are not necessarily limited in its application to the details of construction and the arrangement of the components and/or methods set forth in the following description and/or illustrated in the drawings. The example systems, methods, apparatuses, and/or computer program products are capable of other embodiments or of being practiced or carried out in various ways.

Method of Defining Paths Along a Vascular Tree

Reference is now made to FIG. 1, which is a schematic flowchart of a method of defining vascular centerline paths on an angiographic image, according to some exemplary embodiments of the present disclosure.

In some embodiments, an editing mode of a computer program configured for interactive vascular path definition via user interaction through a user interface is activated. At block 102, in some embodiments, a root position (corresponding, for example, to root positions 401, 501 of FIGS. 4A-4F and 5A-5F) is defined. In some embodiments, the root position is the vascular position visible in the image which is topologically nearest to the region where blood enters or exits the heart. In the coronary arteries, for example, the root position is topologically nearest to the region where blood exits the left ventricle into the aorta. Optionally, the root position is manually defined, for example, by clicking on or touching (via a user interface device) a point in the image; and/or by selecting, moving, and/or confirming an automatically defined root position. Optionally, automatic detection of one or more candidates for the root position is performed, for example, based on the timing and/or location of dye appearance in an image time series immediately after injection; and/or based on morphological criteria such as vascular thickness, branch order and/or orientation, etc.

Figure 2:
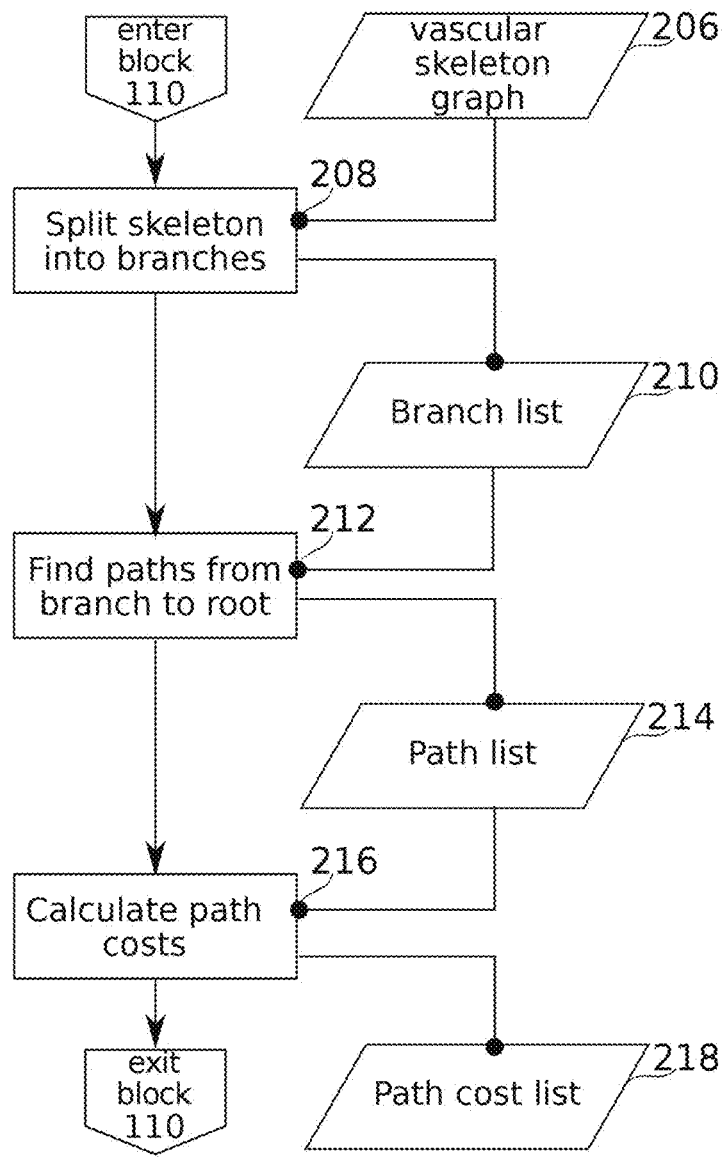
FIG. 2 is a schematic flowchart of a method for generating vascular path options from a vascular image, according to some exemplary embodiments of the present disclosure.

At block 110, in some embodiments, the defined root position is used as an input for the definition of path data including listing of alternative path options and path option costs, for example as described in relation to FIG. 2.

At block 112, in some embodiments, a vascular path representing a path of continuous vascular connection between some point in a vascular tree image and the root position is optionally defined (and/or selected, for example, based on the listing of path alternative path options and path option costs defined at block 110). Examples of the implementation of details of block 112 are described in relation to FIG. 3A.

At block 114, a vascular path representing a previously defined path of continuous vascular connection between some point in a vascular tree image and the root position is optionally edited. Examples of the implementation of details of block 114 are described in relation to FIG. 3B.

At block 104, in some embodiments, a determination is made as to whether or not edit mode is continuing; if not the flowchart exits. Otherwise, flow returns to before block 112 (optionally, to before block 102, to allow redefinition of the root position).

Vascular Paths and Cost Functions

Reference is now made to FIG. 2, which is a schematic flowchart of a method of generating vascular path options from a vascular image, according to some exemplary embodiments of the present disclosure.

The flowchart begins; and at block 208, in some embodiments, a vascular skeleton graph 206 is split into branches. In some embodiments, the vascular skeleton graph is derived from image processing of an angiographic image. Images 400 of FIGS. 4A-4F and 500 of FIGS. 5A-5F are examples of the source images from which the vascular skeleton graph is derived. In some embodiments, the vascular skeleton graph is comprised of vascular centerlines. An example of the extraction of vascular centerlines (which in some embodiments uses anisotropic diffusion, Frangi filtering, and hysteresis thresholding, followed by binary thinning) is described, for example, in relation to block 20 of FIG. 14 of International Patent Publication No. WO2014/111927 to the applicant, filed on Jan. 15, 2014; the contents of which are incorporated herein by reference in their entirety. In some embodiments, the basis of the method used is similar to that introduced by Weickert in "A Scheme for Coherence-Enhancing Diffusion Filtering with Optimized Rotation Invariance" and/or "Anisotropic Diffusion in Image Processing" (Thesis 1996).

At block 208, in some embodiments, the vascular skeleton graph 206 is split into branches. Optionally, this comprises noting pixels at which three or more skeleton segments converge (e.g., pixels with three or more neighbors; optionally, short spurs are excluded from consideration), and assigning these points to be path breaks. Optionally, it is also noted which branches connect to which (connection may be merely apparent, as the branches may also cross one another and/or approach closely enough to appear to merge). The result of the operations of block 208 is branch list 210. It should be noted that the "branches" of branch list 210 are potentially linked into loops, either due to the actual underlying anatomy (for example, the development of shunting vessels), and/or due to apparent connection arising from vascular near approaches and/or crossings at the provided angle and/or resolution of the image.

In some embodiments, branches preserved in the branch list are only those for which a continuously connected route exists to a root position (e.g., root positions 401, 501 of Images 4A-4F and 5A-5F) on the vascular tree. Optionally, the root position is determined, for example, as described in relation to block 102 of FIG. 1.

At block 212, in some embodiments, paths leading from each branch to the defined root position are calculated, for example, by use of a search algorithm. Optionally, there is more than one such path available, for example due to crossings, close approaches, or other ambiguities present in the image, as previously mentioned. Paths that internally include the same vascular segment more than once are optionally excluded from this list (to avoid paths that loop and/or double back on themselves). The data structure resulting from the operations of block 212 comprises path list 214. In some embodiments, path list 214 comprises each non-excluded path identified that extends between the root position and each vascular skeleton segment.

At block 216, in some embodiments, path costs for each path in path list 214 are calculated to produce a path cost list 218. Path cost list 218, in some embodiments, is structured so that members of a potential plurality of paths in path list 214 reaching from any vascular segment to the root can be rank ordered for likelihood of being an actual path of blood flow. Use of path list 214 and/or path cost list 218 is described further in connection with operations of block 112 of FIG. 1, for example as detailed in relation to FIG. 3A.

According to a convention adopted herein, higher cost paths are optionally considered less likely as candidates to be an actual path of blood flow in the vascular anatomy. Path cost criteria are optionally evaluated, for example, to receiving a binary value (0 or 1, for example), a ranked value, and/or a score on a continuous scale. Path cost criteria optionally add, multiply, or are otherwise combined into an overall cost function.

In some embodiments, results of machine learning are used to assign criteria cost values, and/or contribution to overall cost relative to other criteria. In some embodiments, a machine learning technique comprises one or more implementations of decision tree learning, association rule learning, an artificial neural network, inductive logic programming, a support vector machine, cluster analysis, Bayesian networks, reinforcement learning, representation learning, similarity and metric learning, and/or a technique related to machine learning. The machine learning is optionally based on a set of angiographic images which have been separately marked for vascular tree morphology, and/or based on results of self-learning.

Cost Criteria

In some embodiments, path costs recorded in the path cost list 218 are calculated with respect to one or more of the following considerations and/or criteria.

Node Type Classification

Herein, vascular skeleton segment connection points are referred to as nodes. Nodes may be defined as single pixels, or optionally, as regions of larger size (e.g., a radius of 2, 3, 4, 5 or more pixels) within which three or more vascular skeleton segments meet. In some embodiments, the overall cost function which is applicable to a node depends at least in part on a node type classification.

Where two vascular segments happen to cross in an image (e.g. due to being in different planes of the heart image), the vascular skeleton will show four branches arising from approximately the region of a central node. The corresponding vascular skeleton is optionally analyzed as defining a crossing-type node. In some embodiments, where a blood vessel branches, bifurcation is typical. In such cases, the nodes is optionally defined as a junction node from which three vascular skeleton branches arise. Cost function criteria applicable to these two basic node types are optionally differently assigned.

In some embodiments, there are other junction orders which can appear in the path list. For example, a bifurcation may happen to be at the same position as a vascular crossing point. Another situation which potentially arises is where two junction nodes appear so close to one another that they could also be analyzed as four-branched node. Contrariwise, skeletonization artifacts potentially introduce a slight offset to the same blood vessel on either side of a crossing, making it appear more like two adjacent junction-type nodes. Three- and four-branched nodes can also arise where a terminal vascular segment (that is, a vascular segment which is the last segment visible in the image on its branch) happens to have a free end located at or near the position of another vascular segment. Optionally, nodes comprising five, six, or more segments are analyzed as being composed of a suitable combination of junction nodes, crossing nodes, and/or free-end terminations.

In some embodiments, morphological criteria besides branch counts are used in node classification for purposes of cost function assignment. For example, some close sequential bifurcations comprise just one continuously oriented pair of segments, while the other two segments run at a relative sharp angle (e.g., about 90°) relative to one another. In another example, bifurcation angles typically (though not exclusively) display forward-direction (in the direction of arterial flow) acute angles. Backward-branching oblique angles are more likely to signify a crossing-type node. In yet another example, regions of vascular crossings may appear as regions of increased radiopacity (due to the cumulative contribution of two overlapping vascular thicknesses), compared to regions of vascular branching. On the other hand, sudden variations in apparent radiopacity on either side of a node potentially indicate a branching-type node, due to changes in vascular orientation (and corresponding changes in absorbing path length) relative to an axis perpendicular to the plane of the image.

Optionally, for example, for classification of more complex nodes, Murray's principle is applied, wherein $r_p^3 = r_{d_1}^3 + r_{d_2}^3 r_{d_3}^3 + \ldots + r_{d_n}^3$ with $r_p^3$ being the radius of the parent (trunk) branch, and $r_{d_1}^3, r_{d_2}^3, r_{d_3}^3 \ldots r_{d_n}^3$ being the radii of the respective child branches. Optionally, a vascular segment combination which satisfies Murray's principle at some node is assigned a higher probability of representing a branching-type node, with remaining segments assigned higher probabilities of being free-end terminations, or participants in crossing-type node structures.

In some embodiments, the appropriate cost function for the node is dependent on which analysis of the node-type is correct. In some embodiments, node-type determination is subject to probabilistic assignment; e.g., a node is assigned an 80% chance of being a crossing of two vessels, a 15% chance of being a double bifurcation (or trifurcation), and a 5% chance of being a bifurcation in the region of the free end of a terminal vascular segment.

In some embodiments, there is no explicit classification made in the cost function between junction-type and crossing-type nodes (or free ends, or combinations of any of these types); rather, heuristics are adopted which operate on the basic relative vascular morphologies as such. This approach may be suitable, for example, for certain types of machine learning-based implementations like artificial neural networks. Nevertheless, node type provides a convenient organizing concept for purposes of explaining further vascular path cost function criteria.

Continuity and/or Consistency at Crossing-Type Nodes

In some embodiments of the disclosure, continuity of vascular morphology at nodes is used as a basis of cost function value assignment.

The convergence of four vascular skeleton branches considered as a potential crossing-type node is optionally analyzed as defining an a priori choice of three directions to continue in (exit-side) from some fourth direction of approach (entrance-side). In some embodiments, one or more criteria relating to continuity of morphology are applied to determine which exit-side branch is the branch of most likely continuation from a given entrance-side.

One such criterion is vascular radius, wherein the exit-side vascular branch, which is most similar in radius to the entrance-side, receives the correspondingly lowest cost assignment. Optionally, vascular radius is measured as half the apparent width of a filled lumen in the image. Optionally continuity of image intensity values (which is partially, but not only, a function of radius) is also taken into account, e.g., by direct comparison of intensity values. Optionally, principles of densitometry are applied: for example, the blood vessel is modeled as cylinder of a certain radius filled with a substance having a particular concentration and/or coefficient of absorption; and the cost function is based jointly on continuity of radius and absorption properties that satisfy observed intensity values in the image.

In some embodiments, continuity of direction is a criterion: the exit-side vascular segment that is most similar in direction to the entrance-side segment optionally receives the correspondingly lowest cost assignment as its continuation. It is noted that densitometry differences can also arise based on the orientation of blood vessels in the direction perpendicular to the plane of the image; e.g., a blood vessel appears darker when seen more nearly end-on. Thus, continuity of vascular intensity values is optionally a proxy for continuity of vascular direction in this dimension.

In some embodiments, these criteria include one or more further refinements. For example, a criterion of direction applied to a junction may optionally comprise a cost assignment based on the continuing rate and/or direction of angle change before and after a node (e.g., continuation between two segments having a more similar radius of curvature receives a lower cost assignment). This is potentially of particular relevance for vascular segments that are rounding a bulge of the 3-D heart surface through a portion of the vascular image. In some embodiments, a criterion of the cost function favors paths along which vascular width monotonically changes (e.g., increasing in the direction of the root).

In some embodiments, paths from segments A, B, C, D meeting at a junction (particularly a crossing-type junction) are treated as "entangled", such that a low cost for a path leading from A→B correspondingly lowers the cost of the path C→D relative to alternative path C→B. Optionally, a definitive indication by a user during some stage of vascular tree drawing that path A→B is a preferred path of vascular flow is similarly entangled to lowering the cost assignment of path C→D compared to C→B.

Continuity and/or Consistency at Branching-Type Nodes

In some embodiments, where a blood vessel branches, bifurcation is typical. Optionally, a greater branch number, such as trifurcation, is treated as being composed of adjacent bifurcations. In a bifurcation, there is optionally defined a junction node at which there is an a priori choice of two directions to continue in (exit-side) from any third direction of approach (entrance-side). In some embodiments, the heuristic is adopted that the exit-side branch which requires the minimal change in direction through the junction node receives the lower cost assignment.

Optionally, cost scoring based on vascular radius similarity is reduced in its influence on the cost function (e.g., by lower weighting) when a three-way junction node is detected, to account for two thin branches being potentially nearer in size to each other than their mutual trunk. Additionally or alternatively, radius-based cost functions are assigned in a different way for branching-type nodes; e.g., the thickest vascular segment (which generally lies in the direction of the root position) is given the lowest cost score for both of the two thinner branches. Optionally, a cost score assignment is more particularly based on Murray's principle, wherein paths that better satisfy this theoretical relationship are given correspondingly lower cost scores.

Other Criteria

In some embodiments, paths using vascular segments which run in relatively straight and/or continuously arcing lines are optionally scored with lower costs. This is a potential advantage for favoring image features that are "more vascular" in character, as opposed to image features which might end up in the vascular skeleton, but are actually non-vascular in origin. Cost is optionally calculated, for example, based on the total area under the curve (above or below zero) of the derivative of the angle of local vascular segment orientation.

In some embodiments, vascular position in three dimensions is estimated. Optionally, use of this information is part of node classification, and/or used in continuity/consistency cost scoring. In some embodiments, a vascular tree is known a priori to extend across a three-dimensionally curved surface, such as a surface defined by the shape of the heart muscle. In some embodiments, parameters of this curved surface are derived from an image shadow delineating boundaries of the shape being followed. In some embodiments, shapes and/or intensities of the vessels themselves identify shape boundaries. For example, as blood vessels curve to be oriented more inwardly/outwardly from the plane of the image, they potentially begin to appear more radiopaque at some boundary limit as they present a longer absorbing cross-section. Vessel rounding a curve in the third dimension may appear to first approach, and then bend away from, some boundary limit in the 2-D image. In some embodiments, a shell is modeled as comprising two portions, generally occupying different depths, but joined together at such a boundary limit. Optionally, vascular segments are scored for their likely position on the overlying or underlying portion of the shell, while treating the boundary limit as a transition zone. Paths which require abrupt transitions between two different shell portions (particularly away from the boundary limit), are optionally given a higher cost value.

Contrariwise, it is noted that vessels of the same type (artery or vein) which occupy the same anatomical plane may assumed, in some embodiments, to be relatively unlikely to cross over one another. Optionally, where a crossing-type node is identified with high probability (additionally or alternatively, where consistency and continuity suggests a vascular crossing with relatively low associated path cost), this is also used to increase the estimated likelihood that the two different vessels occupy two separated shell portions. Then other vascular segments which directly contact them are also correspondingly more likely to be in the same shell portion, information which is optionally used to disambiguate assignment of path costs across nearby nodes.

Vascular Path Selection and/or Definition

Figure 3A:
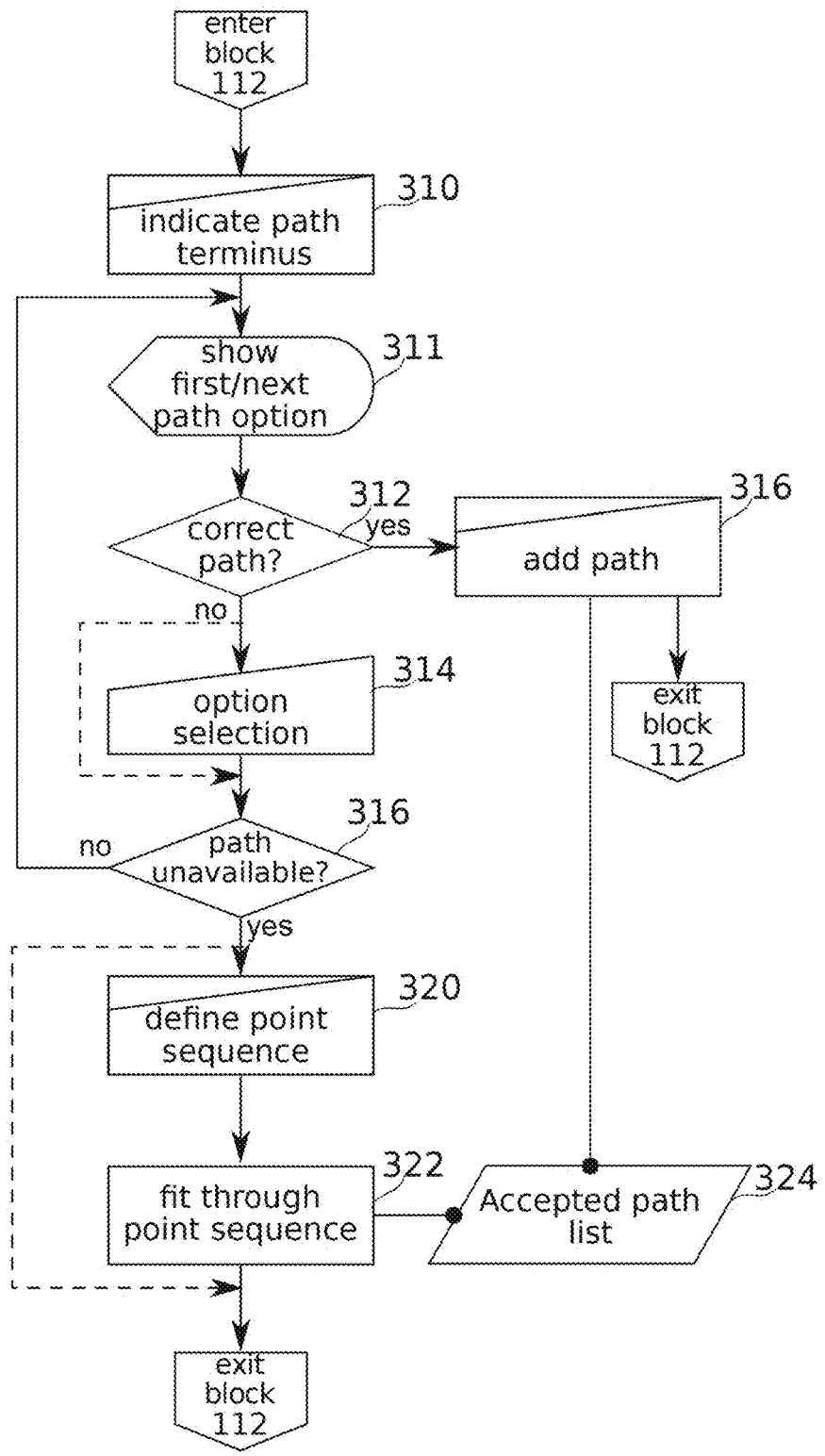
FIG. 3A is a schematic flowchart of a method for selecting and/or defining a particular vascular path option, according to some exemplary embodiments of the present disclosure.
Figure 4A:
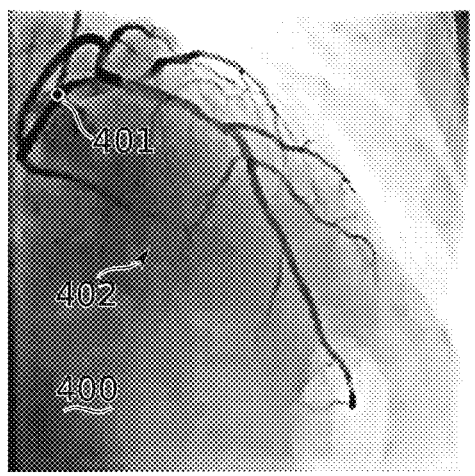
FIGS. 4A-4F schematically illustrate selection of vascular path options, according to some exemplary embodiments of the present disclosure.
Figure 4B:
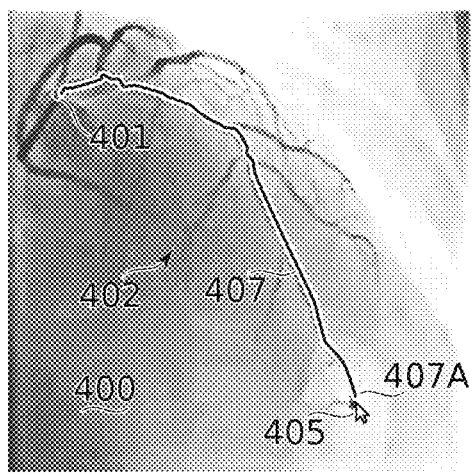

Reference is now made to FIG. 3A, which is a schematic flowchart of a method for selecting and/or defining a particular vascular path option, according to some exemplary embodiments of the present disclosure. In some embodiments, the operations of FIG. 3A correspond to operations occurring within block 112 of FIG. 1. Reference is also made to FIGS. 4A-4F, which schematically illustrate selection of vascular path options, according to some exemplary embodiments of the present disclosure. FIG. 4A shows angiographic image 400 illustrating a portion of a vascular tree 402 (a cardiac vasculature, in the example), including a currently defined root position 401. Contrast of angiographic image 400 is reduced in FIGS. 4B-4F to make other elements more visible.

In some embodiments of the disclosure, there are provided one or more manually guided methods of confirming, selecting, and/or defining vascular tree topology. In this context, there is introduced an "accepted path list" 324. Accepted path list 324 optionally includes paths selected from path list 214, edited paths based on paths in path list 214, and/or paths generated de novo, for example, on the basis of user input. In some embodiments, path cost list 214 is used in determining default selections from path list 214, and/or an order presentation of additional selections from path list 214, as needed.

In connection with block 212 of FIG. 2 herein, the generation of a data structure comprising a path list 214 is described. In some embodiments, path list 214 potentially comprises a number of vascular paths which are "true" vascular paths in the sense that they are isomorphic with a vascular path that blood follows in the actual patient anatomy in flowing between the root position 401 and the distal end of the vascular path. However, there may also be a number of "false" vascular paths in the same path list 214; reflecting ambiguities introduced, for example, by vascular crossing points and/or limitations in vascular image quality. Although path cost list 218 optionally provides a basis for preferring some vascular paths to others, there may nevertheless be cases where circumstances lead to the true vascular path being less preferred. In some embodiments, the true vascular path may not even be available in path list 214; for example, due to contrast dropouts and/or other artifacts which may affect the vascular skeletonization.

Figure 4C:
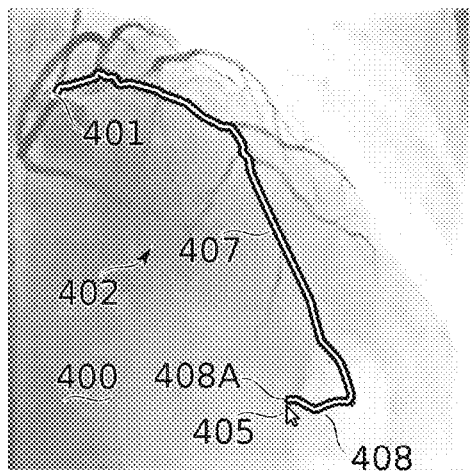

At block 310, in some embodiments, a path terminus is indicated (e.g., by a user). In some embodiments, indication of the path terminus comprises a "hover" cursor input event (e.g., cursor 405 moved into the vicinity of a potential vascular path, and paused long enough to be detected for processing; a long touch on a touch screen, etc.). In some embodiments, another input event indicates the path terminus: for example, a screen tap. In some embodiments, the user indication is referred to a region (e.g., a pixel) on the closest available segment which is represented in path list 214. Optionally, the user indication is referred to the region of the segment which is closest to the position of the indication. For example, vascular path 407 of FIG. 4B extends to a path terminus 407A in the vicinity of cursor 405 at one position. When cursor 405 is moved as shown in FIG. 4C, a different vascular path comprising vascular path 408 appended to vascular path 407 is shown instead, again terminating at path terminus 408A in the vicinity of cursor 405. Optionally, the user indication is referred to the terminal of the segment which is furthest from the root position 401.

For purposes of explanation, the conversion of an indicated path terminus to a path in the accepted path list 324 is primarily presented in terms of manual operations relating to one path at a time. However, it is to be understood that these descriptions also apply, changed as necessary, to the processing of multiple and/or automatically selected paths.

For example, in some embodiments, one or more candidate path termini are detected automatically (for example, at the free ends of vascular skeleton segments which are in continuous connection with the root position 401). Additionally or alternatively, a plurality of path termini are optionally indicated by a user as part of a single input action, e.g., by dragging out a path (by cursor movement, touch input, or otherwise) which crosses among several candidate path termini; the indicated termini being taken as the positions at which the dragged out path intersects segments of the vascular skeleton.

When a plurality of candidate path termini are available, a user is optionally presented with the option to step through candidate path termini (e.g., by a sequence of key presses, finger drags across a touch input screen, scroll wheel movements, or another input), and a selected terminus becomes an indicated path terminus. Optionally, initial paths are defined (and optionally accepted as members of the accepted path list by default) for each of the plurality of candidate path termini.

Upon a first entry into block 311, in some embodiments, the lowest cost available path (based on path cost list 218) from path list 214 that is among those reaching to the indicated path terminus is initially selected for presentation to the user. Optionally, the presentation is differentiated as being active for current definition; for example highlighted with special coloration and/or thickness. It should be noted that although paths from path list 214 are optionally the basis of what is presented, in some embodiments, the actual path shown is derived from an entry in path list 214 by application of an active contour or dynamic "snake" algorithm, for example as described herein.

Figure 4D:
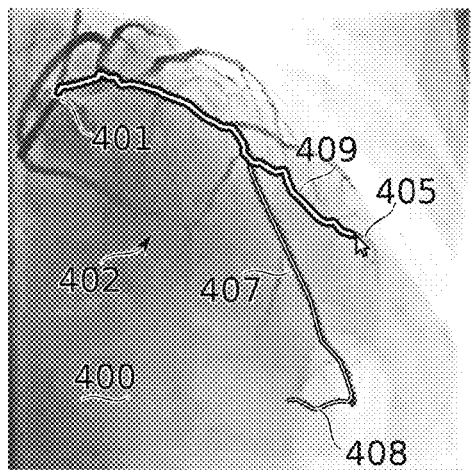
Figure 4E:
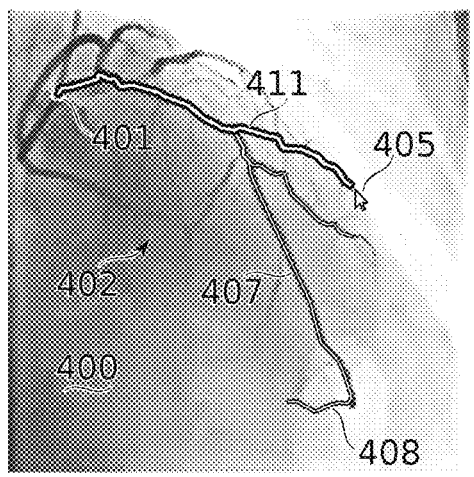
Figure 4F:
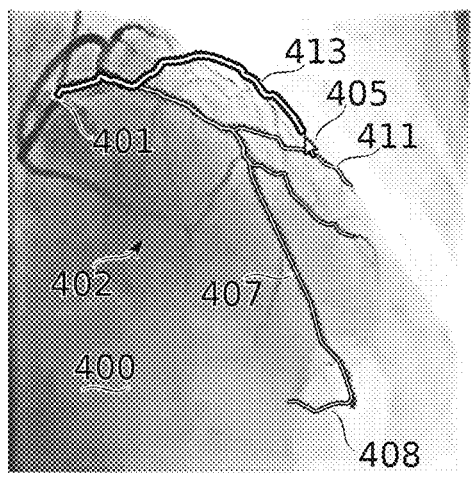

At block 312, in some embodiments, a user determines if the correct path (suitable for use as a "true" vascular path) has been displayed or not. If yes, then the flowchart optionally proceeds with the user issuing a confirmation input (for example, a double click, screen tap, key press, or other input) at block 316. The currently selected path is then added to the accepted path list 324, and the flowchart exits block 112 of FIG. 1. Optionally, accepted paths remain displayed; optionally indicated as deselected, for example, by being drawn thinner, with lower contrast, or by another visual indication. FIG. 4D shows the concatenation of paths 407 and 408 drawn as a member of the accepted path list 324. For the new position of cursor 405, a corresponding new path option 409 is shown. This sequence continues in FIGS. 4E-4F, in which new paths 411 and 414 are created. As presented, each new path is drawn as extending all the way back to root position 401. Alternatively, the display is extended only back as far as the first contact with a previously accepted vascular path. Optionally (and optionally independent of display method), paths are stored in accepted path list 324 as complete paths extending between terminus and root position, as incremental additions to a vascular tree structure, and/or in another format.

Otherwise, if in block 312 the correct path has not been displayed, the flowchart continues; optionally to an option selection event at block 314. In some embodiments, the option selection event comprises movement of a scroll wheel, a touch screen gesture (for example, a sliding motion), a key press, or another user input event. Optionally, this selection is interpreted in software as indicating that the current path display should move to another candidate (e.g. the next candidate available in order of cost as defined in path cost list 218). In a variant of the method, a plurality of vascular path candidates are presented simultaneously for a single pair of end points, and the selection is used to indicate which candidate should be drawn as actively selected. A potential advantage of this variant is to allow more rapid realization that no suitable candidate is available, and/or to allow simultaneous comparison of available options.

At block 316, in some embodiments, the user may decide that no pre-defined path of path list 214 is suitable for the currently indicated path terminus, and proceed to block 320 in order to define a new path manually. Otherwise, in some embodiments, the flowchart returns to block 311, at which the newly selected path candidate is shown.

Figure 5A:
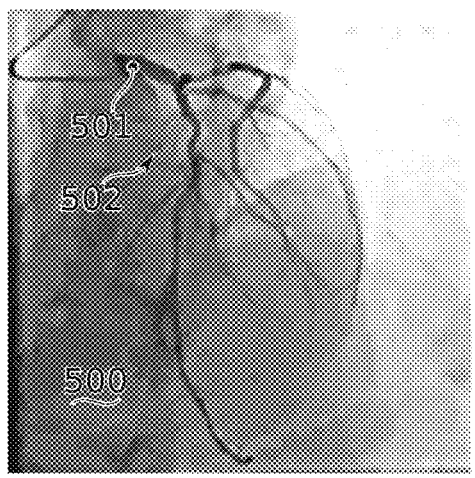
FIGS. 5A-5C schematically illustrate selection from among alternative vascular path options, according to some exemplary embodiments of the present disclosure.
Figure 5B:
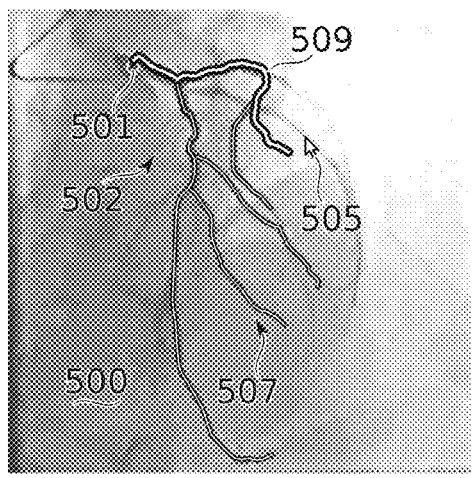
Figure 5C:
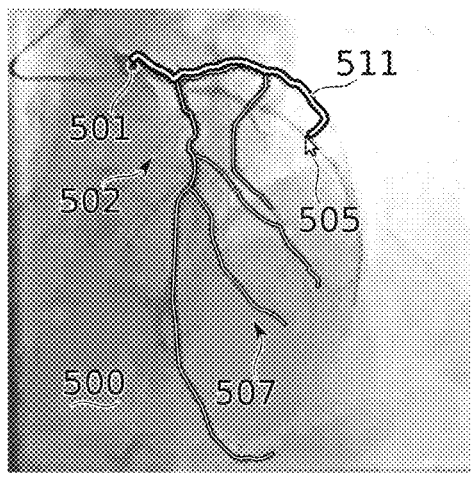

With respect to iteration through blocks 311, 312, and 314, reference is now made to FIGS. 5A-5C, which schematically illustrate selection from among alternative vascular path options, according to some exemplary embodiments of the present disclosure. FIG. 5A shows angiographic image 500 illustrating a portion of a vascular tree 502 (a cardiac vasculature, in the example), including a currently defined root position 501. Contrast of angiographic image 500 is reduced in FIGS. 5B-5F to make other elements more visible. In FIG. 5B, several previously defined paths 507 are shown. Cursor 505 is shown hovering directly over a vascular location, but the suggested path 509 instead terminates some distance away from the cursor on another vascular location. In FIG. 5C, a user has indicated that the next candidate vascular path 511 should be shown, but this vascular path also fails to show what the user intends to add to the accepted path list.

Figure 5D:
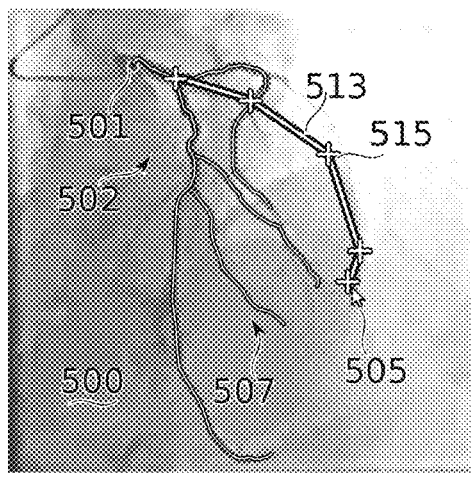
FIGS. 5D-5E schematically illustrate a method of manually defining a vascular path option, according to some exemplary embodiments of the present disclosure.

Finding that the path as intended is unavailable (per block 316), the user optionally proceeds to block 320. With respect to this block, reference is now made to FIGS. 5D-5E, which schematically illustrate a method of manually defining a vascular path option, according to some exemplary embodiments of the present disclosure. FIG. 5D shows a selection formed by a sequence of position indications (clicks made at different positions of cursor 505, for example), with a line segment drawn between each indication. The user has made position indications generally along the intended vascular path. Optionally, root position 501 is considered part of the position indications.

Figure 5E:
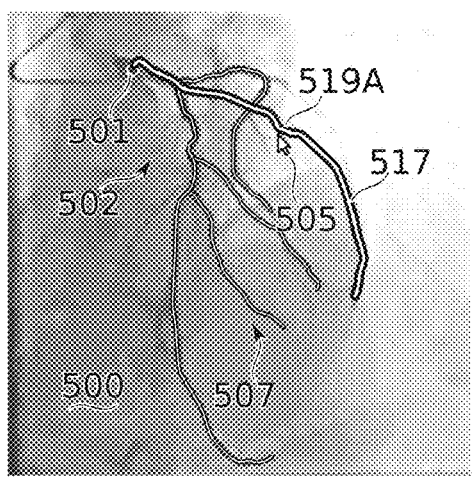

At FIG. 5E, the user has ended the sequence of position indications (for example, with a double click). In some embodiments, this results in the operations of block 322, in which the position indications are used to create a new path definition by a form of fitting between them, for example, as described in relation to an active contour algorithm herein. The resulting vascular path is optionally added to the accepted path to list; and the flowchart of FIG. 3A exits from block 112.

In some embodiments, another method of manually defining a vascular path is used, for example, a variation of the Livewire technique, in which a segment position is optionally drawn live as between clicks defining waypoints ("growing" to meet the cursor position from a previous anchor point), rather than all at once after all waypoints are initially defined.

Active Contour Method for Vascular Paths

In some embodiments of the disclosure, an active contour method, also commonly referred to as a "snake" dynamics method (Kaas et al. 1987) is implemented. In this method, the behavior of the contour, $c(s)=(x(s), y(s))$, is governed by simulated intrinsic and extrinsic forces that are applied on the contour. These forces are derived from a minimization of an energy functional:

$$E = \int [E_{int}(c(s)) + E_{ext}(c(s))] ds \qquad \text{EQU. 1}$$

The internal energy term is:

$$E_{int}(c(s)) = \frac{1}{2}\left(\alpha(s)\left(\frac{dx}{ds} + \frac{dy}{ds}\right)^2 + \beta(s)\left(\frac{d^2x}{ds^2} + \frac{d^2y}{ds^2}\right)^2\right) \qquad \text{EQU. 2}$$

The external energy term $E_{ext}(c(s))$ is implicitly defined by a force field $$\vec{F}(x(s), y(s)) = \gamma(s)\left(\frac{\partial E_{ext}(x(s), y(s))}{\partial x}, \frac{\partial E_{ext}(x(s), y(s))}{\partial y}\right) \qquad \text{EQU. 3}$$

As a force field, there is calculated in some embodiments the GGVF field (Xu and Prince, 1998) over a Frangi-filtered grayscale image (Frangi et al., 1998), although in general any force field can be used.

Active Contours for Initial Path Definition

When a vessel is first defined from the vascular path list 214, the initial input may be taken from a concatenation of pixels in vascular skeleton segments that connect along a selected path. Optionally, coordinates actually used in the path are repositioned to fall at uniform intervals along the vascular path length (actual center-to-center distances of pixels themselves may be non-uniform due to alternating movements in diagonal and cardinal directions). Then, as the active contour method iterates, the vascular path positions are drawn into new positions according to the various force and field terms used. Once the path anneals to a sufficiently stable configuration, the force terms are set to zero, and the process stops.

Optionally, when a vessel is defined by sparsely provided anchor points as described, for example, in relation to FIGS. 5D-5E, the forces acting on the anchor points are set to zero (e.g., $\alpha(s)$, $\beta(s)$, and $\gamma(s)$ are set to zero), so that these point remain fixed. Points interpolated between them (which may initially be provided as straight lines, by spline interpolation, or by another method) are then subjected to non-zero forces (e.g., $\alpha(s)$, $\beta(s)$, and $\gamma(s)$ are set to non-zero values) through a number of iterations of numerically minimizing the energy functionals of (EQU. 2 and EQU. 3) until a sufficiently stable configuration is reached.

Active Contours for Path Editing

Figure 3B:
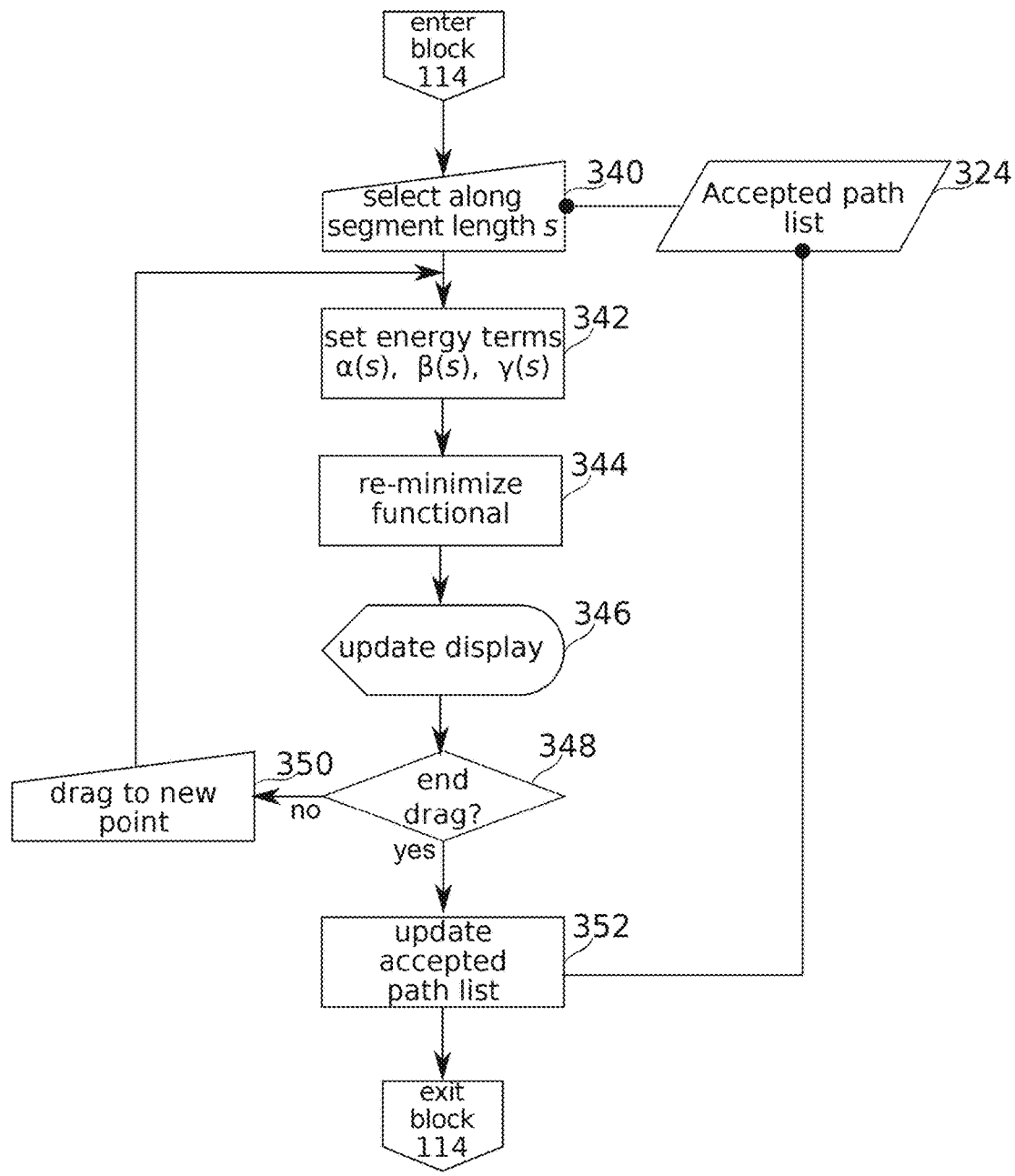
FIG. 3B is a schematic flowchart of a method for manually editing a vascular path, according to some exemplary embodiments of the present disclosure.
Figure 5F:
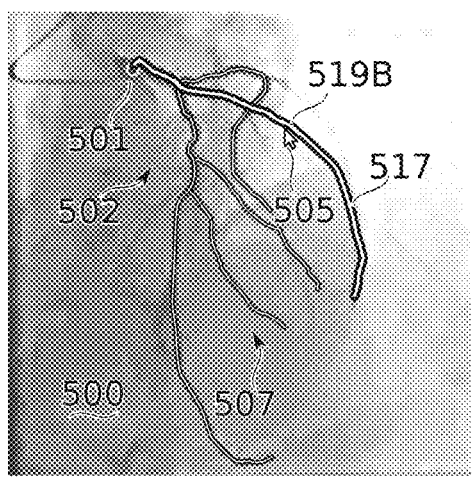
FIG. 5F schematically illustrates manual editing of a vascular path option, according to some exemplary embodiments of the present disclosure.

Reference is now made to FIG. 3B, which is a schematic flowchart of a method of manually editing a vascular path, according to some exemplary embodiments of the present disclosure. FIG. 3B represents an embodiment of the path editing operations of block 114 of FIG. 1. Reference is also made to FIGS. 5E-5F, which schematically illustrate manual editing of a vascular path option, according to some exemplary embodiments of the present disclosure.

At block 340, in some embodiments, a user makes a position selection along length s of a displayed vascular path (which, in some embodiments, is a path from accepted path list 324). In some embodiments, the position selection comprises a button press at some selected position of a cursor, a gesture on a touch screen, or another input method. In subsequent operations, the position selection is taken to define a dragging point, e.g., dragging point 519A of FIG. 5E.

At block 342, in some embodiments, energy terms of $\alpha(s)$, $\beta(s)$ and/or $\gamma(s)$ are set to non-zero only for s within a restricted vicinity of the dragging point. Optionally, the external force field of EQU. 3 is defined to comprise an attractor to the current cursor position, or another position defined by further user interface actions by which the user drags the dragging point to a new location.

At block 344, in some embodiments, the energy functionals of (EQU. 2 and EQU. 3) are numerically minimized, which may result in the displayed vascular path (e.g., path 517 of FIGS. 5E-5F) being displaced around the location of the dragging point.

At block 346, in some embodiments, display of the vascular path 517 is updated.

At block 348, the system determines whether or not the dragging operation is to be ended; for example, based on user input (e.g. release of a button or termination of a touch screen gesture). If not, at block 350 in some embodiments, the user optionally drags the dragging point to a new location, for example, location 519B of FIG. 5F. Otherwise, the edited path 517 is updated in the accepted path list 324, and the flow chart ends (optionally, exiting block 114 of FIG. 1). It should be understood that in some embodiments, the accepted path list is additionally or alternatively updated dynamically during the dragging operation itself.

Vascular Path Definitions from a Plurality of Views

Figure 6:
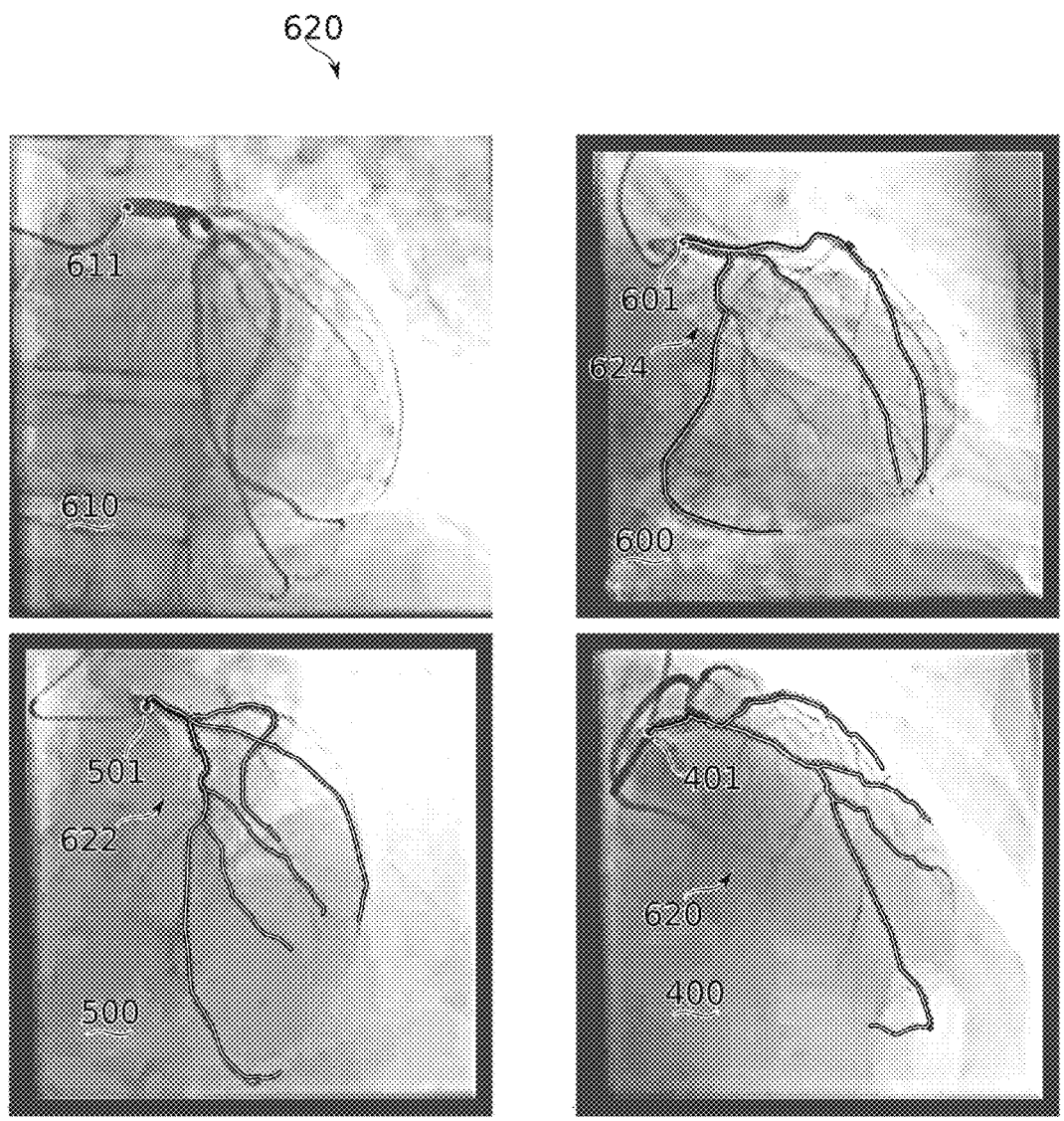
FIG. 6 schematically illustrates a display of path definitions made concurrently on a plurality of different vascular image views, according to some exemplary embodiments of the present disclosure.

Reference is now made to FIG. 6, which schematically illustrates a display 620 of path definitions made concurrently on a plurality of different vascular image views 400, 500, 600, 610, according to some exemplary embodiments of the present disclosure.

In some embodiments, vascular image views 400, 500, 600, 610 each present views from different angles of the same vasculature (e.g., a region of a cardiac vasculature). Partially defined vascular path groups 620, 622, and 624 are shown for views 400, 500, and 600. In some embodiments, homology among vascular image features (homologous image features represent the same anatomical location, optionally from different viewpoints) is established at least in part on the basis of structures identified in one or more of the vascular skeleton graph 216, the branch list 210, the path list 214, and or the accepted path list 324. In some embodiments, the accepted path allows identification of homologous vascular features, optionally without detailed 3-D information: for example, based on considerations of branch numbers and/or positions; root positions 611, 601, 501, 401; and/or relative vascular length. Optionally, basic 3-D information (for example, angle of view specified within about 45°, 90°, or another to greater or lesser amount) helps in identifications by setting general relative orientation correctly, and/or identifying mirror-image views. In some embodiments, fuller 3-D information is available, for example, vascular centerline positions reconstructed based on stereoscopic projection from two or more images into a common 3-D frame of reference (for example as described in International Patent Publication No. WO2014/111930 to the applicant, filed Jan. 15, 2014, the contents of which are incorporated by reference herein in their entirety). Optionally, vascular paths generated with respect to one image view are transformed so that they can be superimposed on one or more alternative image views, based on the reconstructed 3-D frame of reference. In some embodiments, such transforms of vascular skeleton graphs 216, branch list 210, and/or path list 214 are performed, for example to assist in validating image processing results. For example, missing segment portions in path and/or skeleton data from one image can be filled in from data available in views taken from another image. Conversely, spurious segment portions in one image view are optionally identified, for example, based on their absence and/or lack of connection to the root position in other image views.

Figure 7:
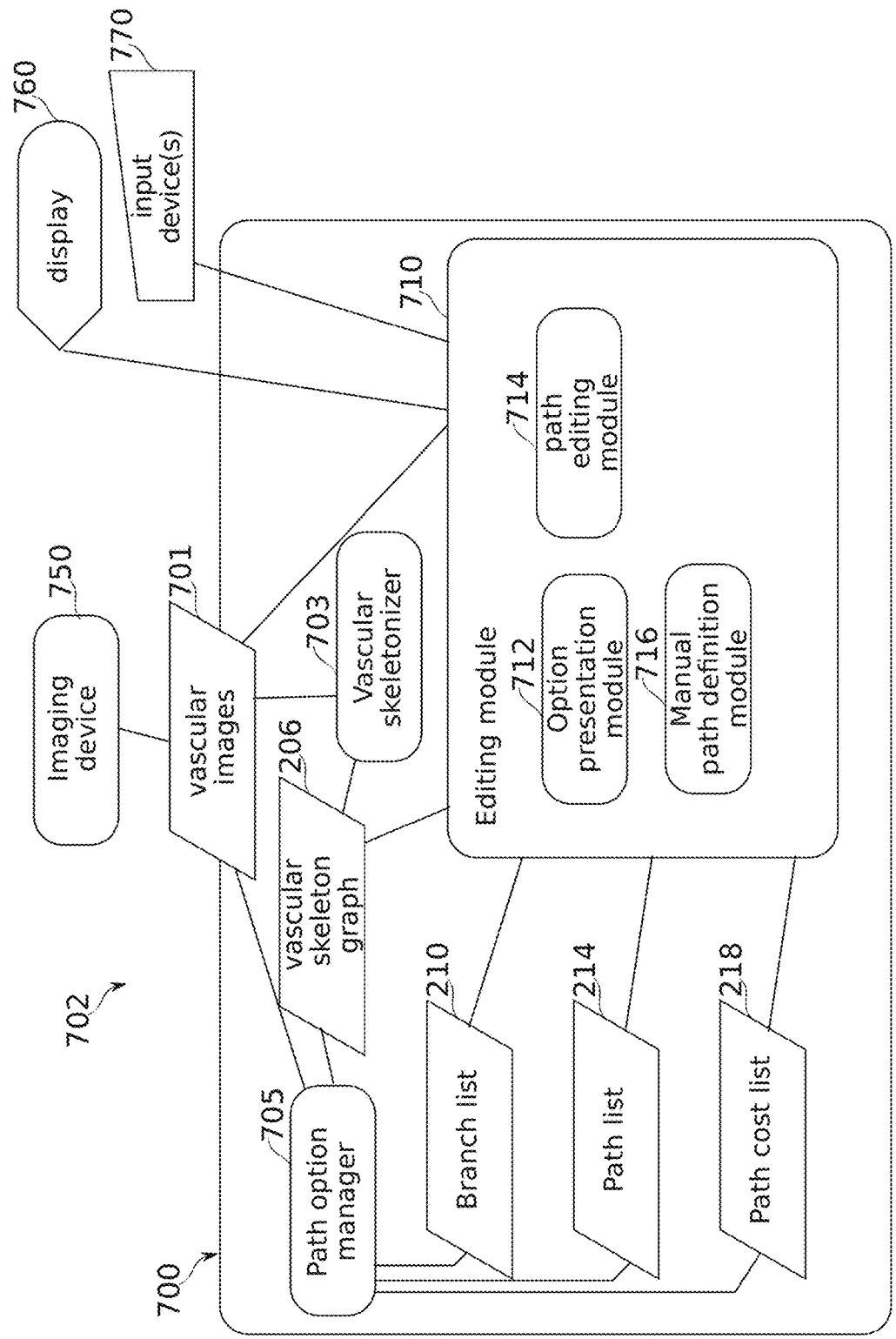
FIG. 7 is a schematic diagram of software modules and data structures implemented in a system for semi-automated segmentation of vascular paths, according to some exemplary embodiments of the present disclosure.

Reference is now made to FIG. 7, which is a schematic diagram of software modules and data structures 700 implemented in a system 702 for semi-automated segmentation of vascular paths, according to some exemplary embodiments of the present disclosure.

Blocks 206, 210, 214, and 218, in some embodiments, comprise data structures generated and/or used by the software modules of the system 702. They correspond, for example, to the correspondingly numbered blocks of FIG. 2. Vascular images 701 are provided from an imaging device 750, which is optionally part of the system 702. Optionally, system 702 is stand-alone, or stand-apart from the imaging device 750, with the images are provided, for example, via a remote network connection.

Block 703, in some embodiments, comprises a vascular skeletonizer, configured for producing a skeletonized representation of vascular segments (skeleton graph), for example as described in relation to block 206 of FIG. 2.

Block 705, in some embodiments, comprises a path option manager. In some embodiments, path option manager 705 comprises software functions for implementing operations of blocks 208, 212, and/or 216 of FIG. 2.

Editing module 710, in some embodiments, comprises sub-modules for handling, for example, operations described in connection with FIGS. 1, 3A, and/or 3B. Optionally, option presentation module 712 and/or manual path definition module 716 implement block 112. Optionally, path editing module 714 implements block 114.

In some embodiments, system 702 additionally comprises display 760 and/or input device(s) 770.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this disclosure may be presented with reference to a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the example systems, methods, apparatuses, and/or computer program products have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features of the example systems, methods, apparatuses, and/or computer program products, which are, for clarity, described in the context of separate embodiments, may also be provided in combination in a single embodiment. Conversely, various features of the systems, methods, apparatuses, and/or computer program products, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

The invention is claimed as follows:

1. A method of segmenting a vascular image into vascular paths for defining paths of blood flow, the method comprising:

receiving, in a processor, the vascular image;

defining, via the processor, first and second targeted vascular path end regions within the vascular image;

segmenting, via the processor, the vascular image to identify the positions of vascular portions in the vascular image;

automatically generating, via the processor, a plurality of vascular path options from the identified vascular portions, each vascular path option defining a potential vascular path that extends between the first and second targeted vascular path end regions;

displaying, via the processor, the plurality of vascular path options registered to the vascular image for selection by a user, each of the displayed vascular path options including the first and second targeted vascular path end regions;

receiving, in the processor, a path option selected by the user for defining a path of blood flow; and adjusting, removing, or adding vascular path options for other targeted vascular path end regions that are within the vascular image based on the path option selected by the user.

2. The method of claim 1, wherein the plurality of paths are automatically generated based on a first set of criteria, and the path option selected by the user is selected based on a second set of criteria.

3. The method of claim 1, further comprising predetermining an order of selection for the vascular path options, wherein the predetermining comprises ranking the vascular path options in an order, based on assessment of a likelihood that each vascular path option corresponds to an actual path of blood flow in blood vessels imaged in the vascular image.

4. The method of claim 3, wherein the predetermining includes applying a cost function that assigns numerical costs to one or more features related to the vascular path options.

5. The method of claim 4, wherein the cost function assigns numerical costs based on features of a plurality of vascular segment centerlines from which the vascular path option is concatenated.

6. The method of claim 5, wherein the features of the plurality of vascular segment centerlines include one or more from the group consisting of centerline orientation, centerline offset, and a count of centerlines extending from a nodal region.

7. The method of claim 3, wherein the cost function assigns numerical costs based on features of the vascular image over which the vascular path option extends.

8. The method of claim 7, wherein the features of the vascular image include one or more of the group consisting of: continuity of vascular segment image intensity, continuity of vascular segment image width, and the position of a relative change in vascular intensity with respect to a nodal region from which three or more vascular segments extend.

9. The method of claim 3, wherein the predetermining includes applying a cost function that assigns numerical costs based on an estimated relative position of a vascular segment image in depth, relative to an axis extending perpendicular to a plane of the vascular image.

10. The method of claim 3, wherein the displaying includes presenting the plurality of vascular path options in a sequential order determined by the order of selection.

11. The method of claim 3, wherein the displaying includes presenting the plurality of vascular path options simultaneously, and the order of selection corresponds to an order in which the vascular path options are displayed as active for selection.

12. The method of claim 1, wherein each vascular path option defines a vascular path which extends through an image region between the first and second targeted vascular path end regions, ending at a vascular region of the image which is nearest to one of the first and second targeted vascular path end positions.

13. A user interface for semi-automatic segmentation of a vascular path, the user interface comprising:

at least one interface module operable to present an automatically generated default vascular path extending between two target end points; and at least one interface module operable to present at least one additional automatically generated vascular path extending between the two target end points, wherein the at least one additional generated vascular path is presented simultaneously with the default vascular path.

14. The user interface of claim 13, further comprising at least one interface module configured to enable definition of at least one way point, and operable to present an automatically generated vascular path extending between the two target end points via the at least one way point.

15. The user interface of claim 14, further comprising at least one interface module operable to modify a previously defined vascular path by dragging a portion of the vascular path to a new location.

16. The method of claim 1, further comprising:

receiving, in the processor, an indication that none of the plurality of vascular path options are acceptable; and enabling, via the processor, a new path to be defined or drawn manually by the user with respect to the vascular image.

17. The method of claim 16, wherein enabling the new path to be defined or drawn includes receiving, in the processor, an indication of the new path based on the user sequentially selecting at least some of the positions of vascular portions.

18. The method of claim 1, wherein at least some of the positions of vascular portions include individual segments connected to a node comprising at least one of crossing vessels, a bifurcation, a double bifurcation, a trifurcation, or a free end.

19. The method of claim 1, further comprising storing, via the processor, the plurality of vascular path options to a path list; and after selection of the path option, causing, via the processor, the other of the plurality of vascular path options for the first and second targeted vascular path end regions to be discarded or designated as being false path options.

20. The method of claim 1, wherein the first targeted vascular path end region or the second targeted vascular path end region includes a root position, and the other of the first targeted vascular path end region or the second targeted vascular path end region includes a terminal position.

* * * * *